(12) United States Patent
Shachar et al.

(10) Patent No.: US 11,130,994 B2
(45) Date of Patent: Sep. 28, 2021

(54) AUTOMATED, CLOUD-BASED, POINT-OF-CARE (POC) PATHOGEN AND ANTIBODY ARRAY DETECTION SYSTEM AND METHOD

(71) Applicant: Autonomous Medical Devices, Inglewood, CA (US)

(72) Inventors: Josh Shachar, Santa Monica, CA (US); Philip Felgner, Irvine, CA (US); Marc Madou, Irvine, CA (US)

(73) Assignee: Autonomous Medical Devices Inc., Santa Monica, CA (US)

( * ) Notice: Subject to any disclaimer, the term of this patent is extended or adjusted under 35 U.S.C. 154(b) by 0 days.

(21) Appl. No.: 16/912,568

(22) Filed: Jun. 25, 2020

(65) Prior Publication Data

US 2021/0180110 A1    Jun. 17, 2021

Related U.S. Application Data

(63) Continuation-in-part of application No. 16/714,421, filed on Dec. 13, 2019.

(51) Int. Cl.

| | | |
|---|---|---|
| *C12Q 1/686* | (2018.01) | |
| *C12Q 1/6809* | (2018.01) | |
| *G01N 15/14* | (2006.01) | |
| *G01N 21/64* | (2006.01) | |
| *G11C 13/00* | (2006.01) | |

(52) U.S. Cl.
CPC ........... *C12Q 1/686* (2013.01); *C12Q 1/6809* (2013.01); *G01N 15/1475* (2013.01); *G01N 21/6428* (2013.01); *G01N 21/6452* (2013.01); *G11C 13/0019* (2013.01); *B01J 2219/00317* (2013.01); *C12Q 2561/113* (2013.01)

(58) Field of Classification Search
None
See application file for complete search history.

(56) References Cited

U.S. PATENT DOCUMENTS

| | | | |
|---|---|---|---|
| 6,252,664 B1 * | 6/2001 | Barbera-Guillem | G01N 21/59 250/461.1 |
| 10,822,379 B1 * | 11/2020 | Dimitrov | A61K 39/395 |
| 10,844,442 B1 * | 11/2020 | Barnhizer | C12Q 1/6804 |
| 10,874,687 B1 * | 12/2020 | Sommadossi | A61P 31/14 |
| 10,948,490 B1 * | 3/2021 | Van Der Werf | G01N 33/54306 |
| 2005/0003459 A1 * | 1/2005 | Krutzik | G01N 33/553 435/7.9 |
| 2014/0045710 A1 * | 2/2014 | Dorak | C12Q 1/6883 506/9 |
| 2017/0138942 A1 * | 5/2017 | Fan | B01L 3/502753 |
| 2021/0088517 A1 * | 3/2021 | Huang | G01N 33/582 |

* cited by examiner

*Primary Examiner* — Ann Y Lam
(74) *Attorney, Agent, or Firm* — Marcus C. Dawes; Daniel L. Dawes

(57) ABSTRACT

The illustrated embodiments of the invention include an automated method of assaying a viral and antibody analyte in a sample in a portable, handheld microfluidic reader having a SAW detector with a minimal mass sensitivity limitation. The automated method includes the steps of automatically performing the assay with the SAW detector with enhanced sensitivity as in Optikus I, but also includes the steps of automatically disposing a second portion of the sample on a microarray, selectively automatically probing the second portion of the sample for antibodies corresponding to the at least one selected virus using the microarray, and automatically reading the microarray using a fluorescent camera to identify antibodies in the second portion of the sample.

10 Claims, 32 Drawing Sheets
(8 of 32 Drawing Sheet(s) Filed in Color)

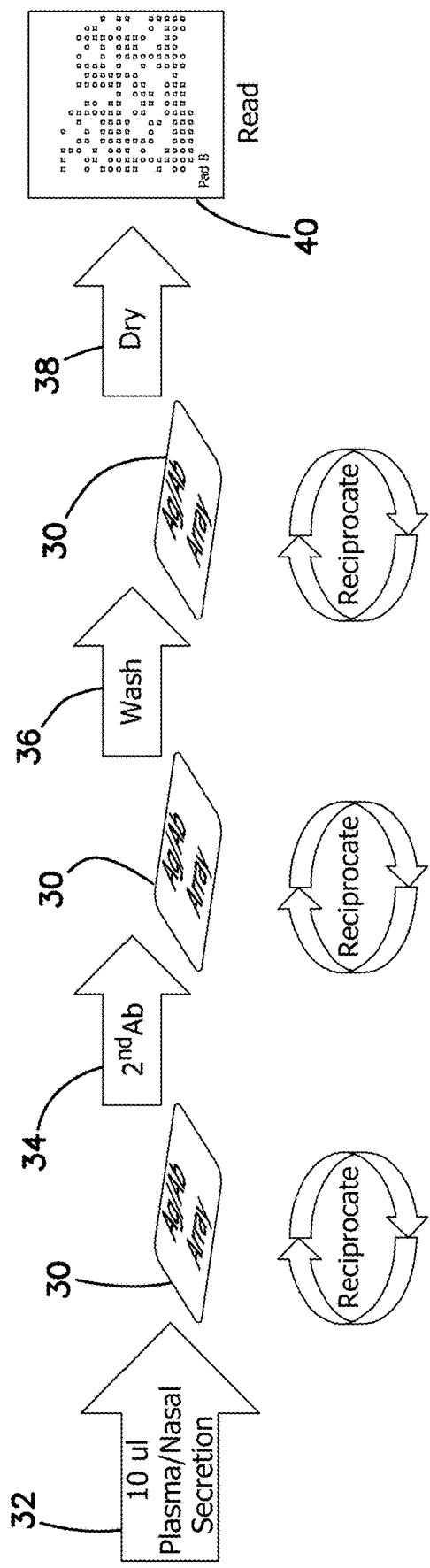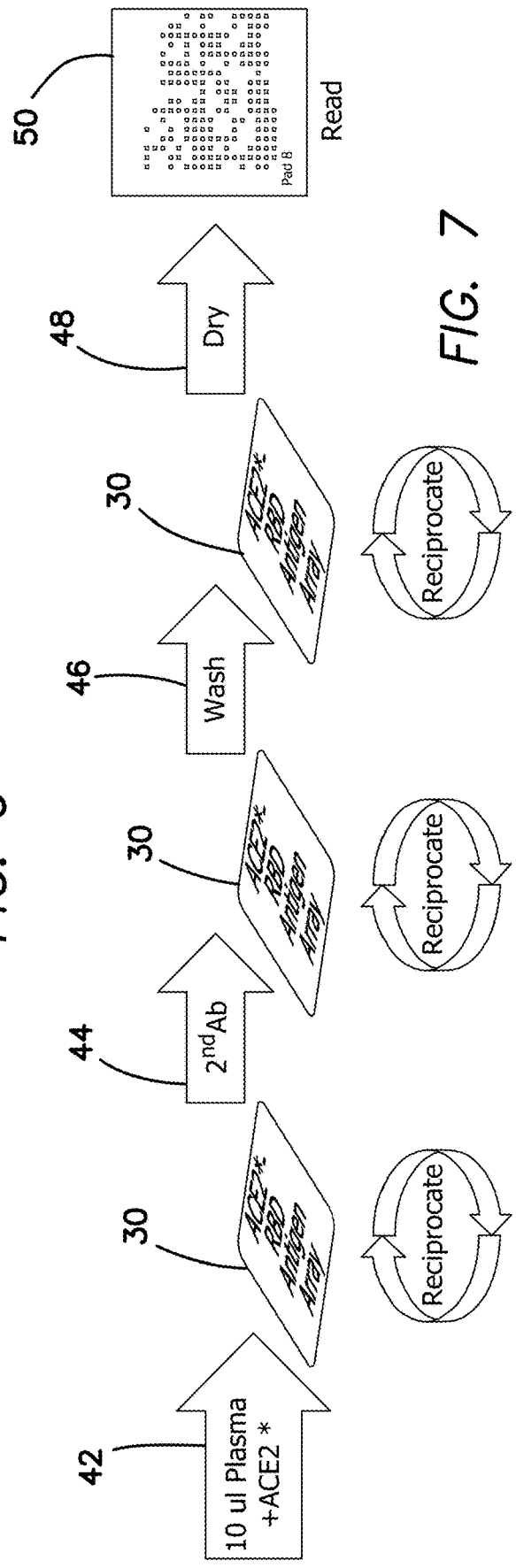

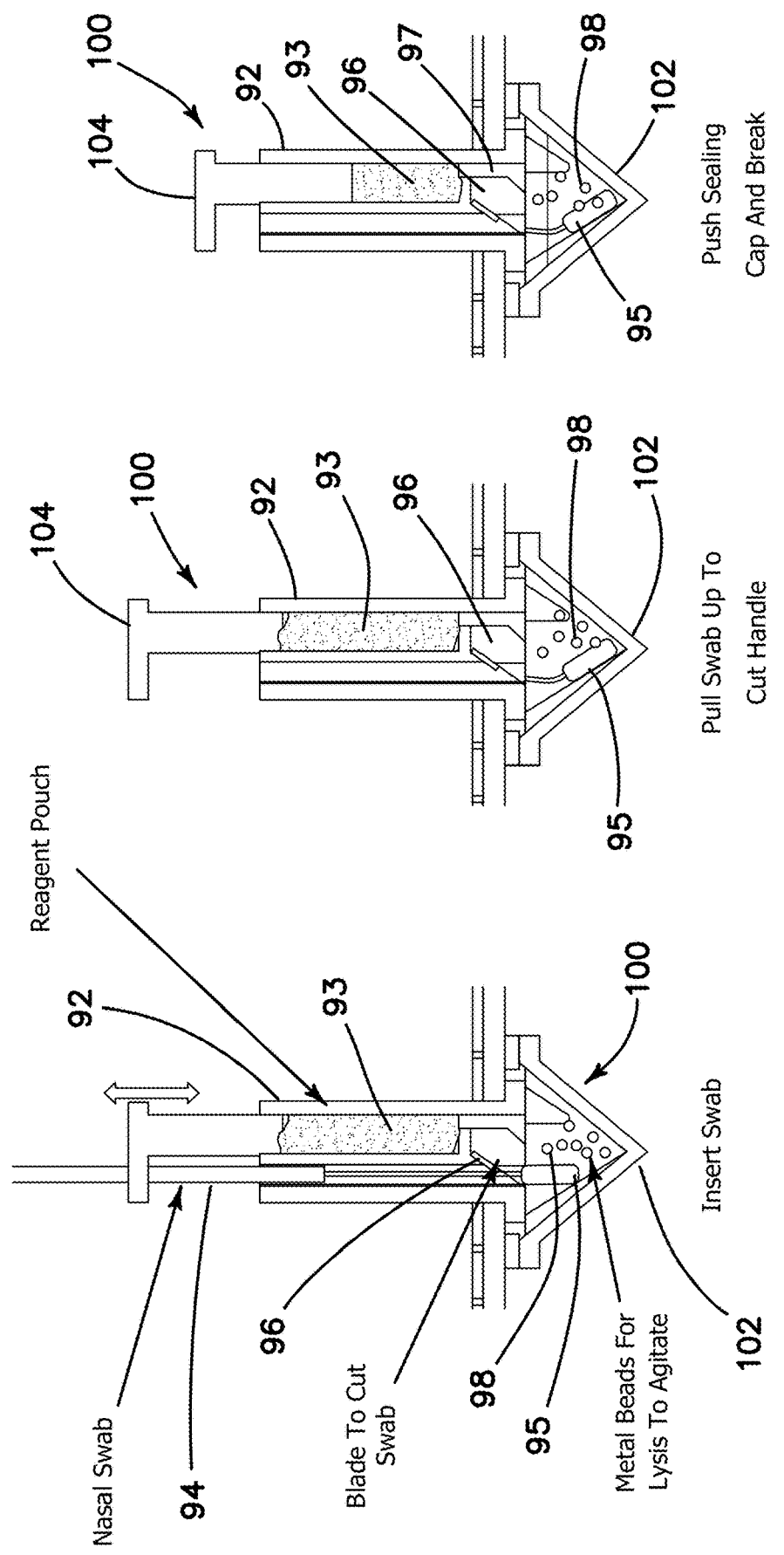

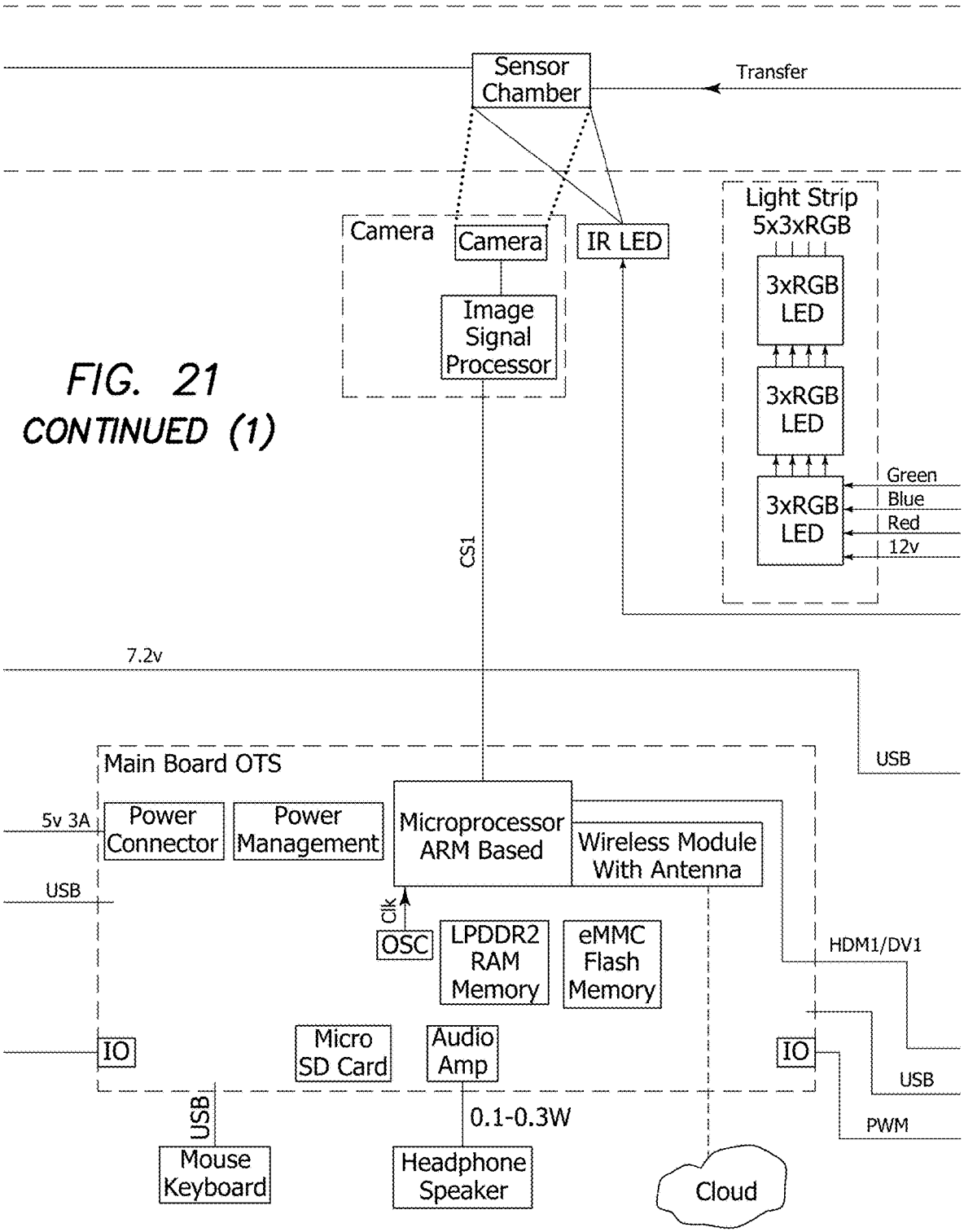
FIG. 21 CONTINUED (1)

CONTINUED(2)

| name | value IgG | ref. IgG | z.score IgG | value IgM | ref. IgM | z.score IgM |
|---|---|---|---|---|---|---|
| SARS.CoV.2.NP | 14551.00 | 1374.91 | 11.38 | 1723.00 | 1420.89 | 0.17 |
| SARS.CoV.2.Pl.pro | 403.50 | 665.28 | -0.40 | 160.72 | 153.55 | 0.12 |
| SARS.CoV.2.S1 | 2853.88 | 1695.89 | 0.81 | 1379.58 | 625.83 | 2.65 |
| SARS.CoV.2.S1.HisTag | 3673.88 | 250.83 | 15.86 | 1598.16 | 87.92 | 11.38 |
| SARS.CoV.2.S1.mFcTag | 7440.38 | 545.47 | 13.16 | 6886.28 | 659.51 | 8.97 |
| SARS.CoV.2.S1.RBD | 7467.88 | 570.75 | 13.01 | 8848.35 | 1273.84 | 10.38 |
| SARS.CoV.2.S1+S2 | 7518.88 | 2233.85 | 2.86 | 3435.40 | 960.59 | 5.86 |
| SARS.CoV.2.S2 | 3452.88 | 1278.24 | 0.97 | 1178.88 | 563.27 | 3.11 |
| SARS.CoV.2.Spike.RBD.Bac | 2254.38 | 888.48 | 3.34 | 2699.38 | 520.37 | 4.73 |
| SARS.CoV.2.Spike.RBD.His.HEK | 2888.88 | 278.67 | 8.48 | 2118.88 | 115.50 | 14.17 |
| SARS.CoV.2.Spike.RBD.rFc | 4881.15 | 839.19 | 3.79 | 2974.38 | 818.89 | 8.03 |
| SARS.CoV_NP | 14829.88 | 2758.58 | 10.81 | 3772.88 | 2415.02 | 0.86 |
| SARS.CoV_Pl.pro | 1888.70 | 583.84 | 1.49 | 282.55 | 423.36 | -0.61 |
| SARS.CoV_S1.HisTag | 679.55 | 1418.36 | -0.85 | 278.00 | 856.47 | -1.87 |
| SARS.CoV_S1.RBD.HisTag | 502.40 | 873.32 | -0.87 | 227.70 | 446.94 | -0.94 |
| SARS.CoV_S1.RBD.rFcTag | 853.15 | 1659.18 | -1.39 | 637.10 | 825.24 | -0.58 |
| MERS.CoV_NP | 501.15 | 1878.35 | -0.55 | 1208.80 | 1566.42 | -0.13 |
| MERS.CoV_S1.AA1.725.His.HEK | 137.65 | 303.19 | -0.85 | 21.95 | 111.41 | -0.81 |
| MERS.CoV_S1.RBD.367.606.rFcTag | 1141.75 | 3405.61 | -1.76 | 776.00 | 1034.58 | -0.47 |
| MERS.CoV_S1.RBD.363.602.mFcTag | 373.45 | 1365.82 | -0.98 | 1247.55 | 2310.08 | -0.82 |
| MERS.CoV_S2 | 4854.88 | 2780.55 | 0.83 | 455.75 | 946.69 | -0.77 |
| DcCoV.HKU23.NP | 917.55 | 2571.47 | -0.97 | 362.05 | 588.45 | -0.51 |
| hCoV.229E.S1 | 3156.40 | 5439.22 | -1.01 | 187.12 | 372.36 | -0.82 |
| hCoV.229E.S1_S2 | 7544.50 | 10036.24 | -1.03 | 615.45 | 1837.28 | -0.53 |
| hCoV.HKU1.HE | 3380.50 | 6264.33 | -0.88 | 1390.10 | 4294.79 | -1.02 |
| hCoV.HKU1.S1_AA1.780 | 1846.75 | 2820.27 | -0.78 | 53.15 | 180.58 | -1.23 |
| hCoV.HKU1.S1_AA13.758 | 988.35 | 3012.07 | -0.94 | 251.50 | 422.75 | -1.05 |
| hCoV.HKU1.S1_S2 | 6788.38 | 4890.55 | 0.95 | 638.55 | 1013.67 | -1.37 |
| hCoV.NL63.S1 | 1281.60 | 1859.04 | -0.52 | 124.70 | 253.78 | -0.85 |
| hCoV.NL63.S1_S2 | 2030.80 | 3302.70 | -1.17 | 394.80 | 1036.94 | -0.77 |
| hCoV.OC43.HE | 1293.10 | 3992.88 | -1.11 | 163.25 | 447.21 | -1.01 |
| hCoV.OC43.S1 | 212.90 | 363.06 | -0.74 | 67.05 | 223.34 | -1.17 |
| hCoV.OC43.S1_S2 | 13497.38 | 7958.39 | 2.01 | 941.28 | 1169.18 | -0.61 |
| Flu.B_Mal.HA1 | 7894.25 | 8568.08 | -0.23 | 194.90 | 436.99 | -0.46 |
| Flu.B_Mal.HA1+HA2 | 11362.85 | 11918.87 | -0.24 | 446.80 | 515.83 | -0.12 |
| Flu.B_Phu.HA1 | 7388.88 | 6356.85 | 0.32 | 175.35 | 332.97 | -0.62 |
| Flu.B_Phu.HA1+HA2 | 10142.05 | 11823.48 | -0.87 | 858.40 | 1997.51 | -0.56 |
| Flu.H1N1.HA1 | 1731.10 | 4421.63 | -1.03 | 352.75 | 468.13 | -1.12 |
| Flu.H1N1.HA1+HA2 | 18887.75 | 10697.92 | 0.10 | 1187.38 | 576.35 | 0.88 |
| Flu.H3N2.HA1 | 13223.88 | 8603.17 | 1.17 | 280.70 | 336.37 | -0.24 |
| Flu.H3N2.HA1+HA2 | 13491.38 | 11237.43 | 0.78 | 896.30 | 1194.50 | -0.58 |
| Flu.H5N1.HA1 | 1845.55 | 3725.37 | -0.96 | 931.05 | 1504.46 | -0.82 |
| Flu.H5N1.HA1+HA2 | 7285.50 | 9349.40 | -0.63 | 1888.88 | 1730.49 | 0.15 |
| Flu.H7N9.HA1 | 654.45 | 1138.48 | -0.59 | 82.85 | 117.85 | -1.23 |
| Flu.H7N9.HA1+HA2 | 838.35 | 1501.44 | -0.58 | 16.00 | 103.03 | -2.19 |
| hAdV3.Fiber | 3106.70 | 5882.67 | -0.62 | 820.25 | 867.55 | -0.10 |
| hAdV3.Penton | 2758.50 | 3406.34 | -0.35 | 798.30 | 604.49 | 0.13 |
| hAdV4.Fiber | 4187.88 | 3940.21 | 0.06 | 519.55 | 840.58 | -0.33 |
| hAdV4.Penton | 1466.70 | 2341.25 | -0.44 | 460.85 | 640.63 | -0.46 |
| hMPV.A_G.52N.229N | 603.80 | 1741.45 | -1.59 | 496.10 | 616.97 | -0.39 |
| hMPV.B_F.280D.490G | 275.70 | 746.49 | -0.91 | 303.00 | 452.87 | -0.47 |
| hMPV.B_G.52D.238S | 550.40 | 1018.13 | -0.44 | 197.10 | 474.71 | -0.75 |
| hPIV.1.12C3_F | 5352.15 | 7393.48 | -0.63 | 788.92 | 1315.02 | -0.93 |
| hPIV.1.12C3_H | 4205.50 | 7259.00 | -1.50 | 1081.15 | 2833.11 | -1.15 |
| hPIV.3.2010_H | 6143.55 | 7617.24 | -0.76 | 840.30 | 1376.41 | -0.93 |
| hPIV.4.b.2016_H | 1839.00 | 4052.51 | -1.16 | 811.40 | 1287.62 | -0.90 |
| RSV.A.F | 6134.12 | 9708.27 | -1.86 | 473.80 | 1159.34 | -1.17 |
| RSV.A.G | 4918.20 | 9280.15 | -1.93 | 855.55 | 829.59 | 0.57 |
| RSV.B.F | 10774.30 | 11856.42 | -0.49 | 1038.20 | 1528.28 | -0.39 |
| RSV.B.G | 8945.12 | 11369.40 | -0.87 | 1988.38 | 782.25 | 0.88 |

Fig. 26

| N | Antigen Combination | IgG AUC | IgG Spec | IgG Sens |
|---|---|---|---|---|
| 1 | SARS-CoV-2_S1+S2 | 0.975 | 0.987 | 0.889 |
| 1 | SARS-CoV-2_NP | 0.975 | 0.961 | 0.889 |
| 1 | SARS-CoV-2_S2 | 0.951 | 0.921 | 0.833 |
| 1 | SARS-CoV_NP | 0.957 | 0.974 | 0.833 |
| 1 | SARS-CoV-2_S1 (mFcTag) | 0.88 | 0.987 | 0.667 |
| 1 | MERS-CoV_S2 | 0.873 | 0.763 | 0.889 |
| 1 | SARS-CoV-2_S1-RBD | 0.849 | 0.947 | 0.833 |
| 2 | SARS-CoV-2_NP ; MERS-CoV_S2 | 0.988 | 0.934 | 1 |
| 2 | SARS-CoV-2_S1+S2 ; SARS-CoV-2_NP | 0.988 | 0.963 | 0.947 |
| 2 | SARS-CoV-2_S1+S2 ; SARS-CoV_NP | 0.975 | 0.974 | 0.889 |
| 2 | SARS-CoV-2_S2 ; SARS-CoV_NP | 0.994 | 1 | 0.944 |
| 3 | SARS-CoV-2_NP ; SARS-CoV-2_S2 ; SARS-CoV_NP | 0.988 | 1 | 0.944 |
| 3 | SARS-CoV-2_S1+S2 ; SARS-CoV-2_NP ; SARS-CoV_NP | 0.981 | 1 | 0.889 |
| 3 | SARS-CoV-2_S1+S2 ; SARS-CoV-2_S2 ; SARS-CoV_NP | 0.975 | 1 | 0.889 |
| 3 | SARS-CoV-2_S1+S2 ; SARS-CoV_NP ; SARS-CoV-2_S1, (mFcTag) | 0.969 | 0.961 | 0.889 |
| 3 | SARS-CoV-2_S2 ; SARS-CoV_NP ; MERS-CoV_S2 | 0.988 | 1 | 0.944 |
| 3 | SARS-CoV-2_S2 ; SARS-CoV_NP ; SARS-CoV-2_S1, (mFcTag) | 0.994 | 1 | 0.944 |
| 4 | SARS-CoV-2_S1+S2 ; SARS-CoV-2_NP ; SARS-CoV-2_S2 ; SARS-CoV_NP | 0.981 | 1 | 0.944 |
| 4 | SARS-CoV-2_S1+S2 ; SARS-CoV-2_NP ; SARS-CoV_NP ; SARS-CoV-2_S1-RBD | 0.975 | 1 | 0.833 |
| 4 | SARS-CoV-2_S1+S2 ; SARS-CoV-2_S2 ; SARS-CoV_NP ; SARS-CoV-2_S1, (mFcTag) | 0.981 | 0.987 | 0.944 |
| 4 | SARS-CoV-2_S1+S2 ; SARS-CoV_NP ; MERS-CoV_S2 ; SARS-CoV-2_S1-RBD | 0.975 | 1 | 0.944 |
| 4 | SARS-CoV-2_S2 ; SARS-CoV_NP ; SARS-CoV-2_S1, (mFcTag) ; SARS-CoV-2_S1-RBD | 0.988 | 1 | 0.944 |

Fig. 27

AUTOMATED, CLOUD-BASED, POINT-OF-CARE (POC) PATHOGEN AND ANTIBODY ARRAY DETECTION SYSTEM AND METHOD

This application is a continuation-in-part and claims priority to, and the benefit of the earlier filing date of: U.S. patent application entitled, APPARATUS AND METHOD FOR OVERCOMING MINIMAL MASS SENSITIVITY LIMITATIONS IN A SHEAR HORIZONTAL SURFACE ACOUSTIC WAVE BIOSENSOR filed on Dec. 13, 2019, Ser. No. 16/714,421, pursuant to 35 USC 120, the contents of all of which are incorporated herein by reference (hereinafter defined as the "incorporated specification").

A portion of the disclosure of this patent document contains material which is subject to copyright or mask work protection. The copyright or mask work owner has no objection to the facsimile reproduction by anyone of the patent document or the patent disclosure, as it appears in the Patent and Trademark Office patent file or records, but otherwise reserves all copyright or mask work rights whatsoever.

BACKGROUND

Field of the Technology

The invention relates to the field of point-of-care (POC) pathogen and multiplexed pathogen antibody array detection platforms and methods, and in particular to CPC C40B 60/12.

Description of the Prior Art

Over the past decades, rising numbers of emerging infectious diseases have caused serious societal and economic impact worldwide. In particular, rural third-world communities experience high exposure to infectious diseases, but also face numerous challenges in healthcare access. Nevertheless, pathogens do not know country boundaries and new disease outbreaks anywhere affect people everywhere. Expert-curated knowledge, software and services to support the interpretation of medical diagnostic test results from a worldwide interconnected point-of-care network that tracks and prevents fast spreading infectious disease pandemics is the only way mankind can expect to maintain vibrant economies and highly mobile societies.

What is needed is an apparatus and method which addresses some of the most urgent requirements to establish disease screening, interpretation and prevention goal by using the current COVID-19 pandemic as a most urgent target. Coronaviruses are enveloped positive-sense RNA viruses that are distributed broadly among humans, other mammals, and birds and cause respiratory, enteric, hepatic, and neurologic diseases. Although there are six known species of this virus that are known to infect humans, only four are prevalent and usually cause cold-like symptoms: 229E, OC43, NL63 and HKU1. The other two species of viruses, severe acute respiratory syndrome coronavirus (SARS-CoV) and Middle East respiratory syndrome coronavirus (HERS-CoV) are zoonotic viruses and caused major pandemic incidents in 2002-2003 and 2012. The global coronavirus pandemic, of which the first cases were detected and reported in late 2019, is the result of a novel coronavirus, named SARS-CoV-2 by the World Health Organization (WHO) that causes the disease COVID-19. The viral surface proteins (spike, envelope and membrane) are embedded in a lipid bilayer envelope derived from the host cell. The single-stranded positive-sense viral RNA is associated with the nucleocapsid protein as shown in FIG. 17.

The current POC COVID-19 detection platforms fall into four categories: 1) Detection Methods for SARS-CoV-2: 2) ELISA, Immunofluorescence Assays, 3) RT-qPCR and 4) Chest X-rays. Chest X-rays are not practical for a widespread POC test.

Enzyme-Linked Immunosorbent Assay—ELISA.

Serological tests measure antibodies in blood from people who have been exposed to the virus. The ELISA blood tests check for immunoglobulin G (IgG) that results from a past or recent exposure to corona virus disease 2019 (COVID-19). The human body produces IgG antibodies as part of the immune response to the virus. It usually takes around 10 to 18 days to produce enough antibodies to be detected in the blood. Additionally, ELISA blood tests can look for Immunoglobin M (IgM) antibodies, which are the first antibodies to appear after an individual is exposed to an antigen but which disappear once the antigen is no longer present. ELISA that looks at IgG and IgM simultaneously can paint a picture about diseases a patient is currently fighting, and diseases the patient has already had and to which the patient has developed an immunity.

The samples typically used are blood samples that—in general—are more reliably collected than nasal or throat swab samples (used in test types 2 and 3 above). But with blood samples, handling, storage, and centrifugation to separate serum from plasma are additional steps required that may introduce errors. If antibodies are found in a serological test sample, direct immunoassays (see test type 2) or DNA tests (see test type 3) are performed to establish if the virus itself is still present in the patient's body.

Immunofluorescence Assays.

These assays have been used extensively to directly detect a variety of viral antigens. Immunofluorescence uses antibodies to detect viral antigens in tissue sections or infected cells. Infected cells such as those from the mucous membrane of the upper respiratory tract or cells that are present in the mucus aspirated from the nasopharynx are used and are collected using a swab. Immunofluorescence assays use a fluorescent label that is conjugated to the antiviral antibody, which is known as direct immunofluorescence or to an anti-antibody, known as indirect immunofluorescence. The amount of binding of the antibody to the antigen is directly correlated with the amount of fluorescence produced source.

We have introduced an alternative direct label free virus detection technology based on a SAW sensor. See the incorporated specification. The sensor utilizes a surface acoustic wave biosensor (SAW) for direct COVID-19 detection. In the past, the SKC SAW sensor has successfully detected multiple high-profile bacteria and viruses, including Ebola, HIV, and anthrax. Over the last two years, we have significantly improved the sensitivity and detection capability of the SAW biosensor. Antibodies for Sars-Cov-2 are immobilized on the SAW surface and the response as a function of concentration is being evaluated. A rapid (<12 minutes), point-of-care diagnostic test for detection of COVID-19 from nasal swab samples.

The use of swabs produce a significant number of false negatives, not necessarily because of insensitive detection methodology, but because the samples can't be reproducibly collected from the nasal passage. There is variation between practitioners who collect the samples and there is also variation in the amount of virus that is present in the nose. Another key drawback is that these tests only give a positive result when the virus is still present. The tests can't identify people who went through an infection, recovered, and cleared the virus from their bodies.

Real Time Quantitative Polymerase Chain Reaction—RT-qPCR.

Direct pathogen detection based on rapid DNA amplification. PCR is used to measure the quantity of genetic material (DNA or RNA) in a sample and involves the use of Taq polymerase, which amplifies a short specific part of the template DNA in temperature cycles. In each cycle, a number of small specific sections of DNA is doubled which leads to exponential amplification of targets. The number of cycles in a PCR experiment is usually between 12-45 cycles. Reverse-transcriptase PCR (RT-PCR) is used to detect RNA, as the RNA is reverse transcribed to DNA. In RT-qPCR, the same method occurs with the exception of two factors; i) the amplified DNA is fluorescently labelled and ii) the amount of fluorescence released during amplification is directly linked to the amount of the amplified DNA source. One-step RT-qPCR detection kits are useful for the in vitro detection of COVID-19 using respiratory specimens-nasal swabs. Examples of POC product includes the Abbott corona virus test using a testing instrument under the brand, ID NOW.

What is needed is an approach which overcomes the problems associated with currently available COVID-19 diagnostic or testing equipment.

BRIEF SUMMARY

The illustrated embodiments of the invention are directed to an automated cloud-based system in which a handheld, field-portable diagnostic instrument capable of automatically performing laboratory-grade diagnostic tests for viral pandemic infections is used. After taking the biosample and disposing it in the handheld, field-portable diagnostic instrument, all further steps of sample preparation and testing are automatically performed without the need for human intervention and associated delay. The sample is tested, results generated, analyzed by artificial intelligence or an expert system, communicated to storage databases, communicated to the tested subject and communicated to associated health care providers within tens of minutes of the test without the necessity or delay of human or further medical intervention. Only in this manner is it possible to provide reliable pandemic testing and reporting of hundreds of millions of subjects, which is a necessary capability if a global pandemic is to be contained or controlled.

The illustrated embodiments of the invention include a method of assaying a viral and antibody analyte in a sample in a portable, handheld microfluidic reader having a detector with a minimal mass sensitivity limitation. The method includes the steps of: inserting the sample in the reader; capturing the analyte from a first portion of the sample with a first antibody having a DNA tag attached thereto and with a second antibody having an attached magnetic nanoparticle (MNP), where a sandwich is formed including the first and second antibodies, the analyte, the MNP and the DNA tag; replicating the DNA tag using isothermal amplification to a predetermined amount of DNA tags sufficient to overcome the minimal mass sensitivity limitation of the detector by providing an amount is reliably detectable by a detector; measuring the amount of replicated DNA tags using the detector to detect at least one selected virus; disposing a second portion of the sample on a microarray; selectively probing the second portion of the sample for antibodies corresponding to the at least one selected virus using the microarray; and reading the microarray using a fluorescent camera to identify antibodies in the second portion of the sample.

The step of selectively probing the second portion of the sample for antibodies corresponding to the at least one selected virus using the microarray includes the steps of: incubating the second portion of the sample on the microarray for a predetermined amount of time; disposing fluorescence labelled secondary Ab; washing the microarray; and drying the microarray. The step of reading the microarray using a fluorescent camera to identify antibodies in the second portion of the sample detects Ig isotypes in the second portion of the sample by generating a color image of the microarray. The method further includes the step of communicating the color image of the microarray to the cloud for analysis and/or data processing.

In the embodiments where the microarray has been provided with DNA spots of receptor binding domain (RBD) of spike protein, the step of selectively probing the second portion of the sample for antibodies corresponding to the at least one selected virus using the microarray includes the steps of: performing a neutralizing antibody assay using the microarray provided with DNA spots of receptor binding domain (RBD) of spike protein and fluorophore labelled ACE2 and another fluorophore labelled secondary antibody against human IgG for detection of RBD antibody; washing the microarray; drying the microarray. The step of reading the microarray using a fluorescent camera to identify antibodies in the second portion of the sample generates a color image of the microarray with at least two different colors, one color for RBD antibody present in the second portion of the sample and a second color for ACE2, the second portion of the sample without neutralizing antibodies or RBD antibodies being detected with ACE2 fluorescence, while samples with RBD antibodies or increasing amount of neutralizing antibodies that interfere with ACE2-RBD binding being detected with a decreasing amount of ACE2 fluorescence. In the absence of RBD antibodies, the amount of ACE2 fluorescence can be quantified for relative neutralizing activity. The method further includes the step of communicating the color image of the microarray to the cloud for analysis and/or data processing.

The microarray contains normalizing fluorophore controls which will fluoresce with a known intensity. Three spots are 100% intensity, three spots are 50% intensity, and three spots are 0% intensity. By taking measurements of these 9 spots, a normalization curve can be created which allows against which the remaining test dots to be compared and plotted.

The step of selectively probing the second portion of the sample for antibodies corresponding to the at least one selected virus using the microarray further includes the step of micro-mixing the second portion of the sample using reciprocation in which centrifugal acceleration acting on a liquid element first generates and stores pneumatic energy that is then released by a reduction of the centrifugal acceleration, resulting in a reversal of direction of flow of the liquid, and applying an alternating sequence of high and low centrifugal acceleration to the second portion of the sample to maximize incubation/hybridization efficiency between antibodies and antigen macromolecules during the incubation/hybridization.

The illustrated embodiments also include a portable, handheld microfluidic reader for assaying an analyte in a sample. The reader having a rotatable microfluidic disc or rotor and includes: a sample inlet defined in the disc into which the sample is inserted; a mixing chamber defined in the disc and selectively communicated to the sample inlet and provided with a first antibody for capturing the analyte having a DNA tag attached thereto; an amplification chamber defined in the disc selectively communicated to the mixing chamber provided with a second antibody for capturing the analyte attached to a surface or having a magnetic nanoparticle (MNP) attached thereto, where a sandwich including the surface or MNP, first and second antibodies, the analyte and the DNA tag is formed in the amplification chamber; and for replicating the DNA tag using isothermal amplification to produce a predetermined amount of DNA tags; a detector selectively communicated to the amplification chamber and provided in the disc for measuring the amount of replicated DNA tags; a reaction chamber for receiving a second portion of the sample; a microarray disposed in the reaction chamber for selectively probing the second portion of the sample for antibodies corresponding to the at least one selected virus using the microarray; and a fluorescence camera for reading the microarray to identify antibodies in the second portion of the sample.

The detector includes an LED for exciting the fluorophore on the microarray on disc CD-1 for making a measurement and includes a CMOS camera for capturing of photons emitted by the excited fluorophore. The device also includes two filters with distinctive wavelength bands, one between the fluorophore and the microarray (750 nm), and one between the microarray and the CMOS camera (790 nm). The bands of the two filters are separate and do not share any overlap in the electromagnetic spectrum thus preventing any scattered light from the emitting LED from impacting the measurement made by the CMOS camera.

The detector includes a surface wave acoustic (SAW) detector for use with CD-2. The detector contains all of the necessary RF signal generators and interposers which interfaces the device and the disk, so that an RF measurement can be made on the SAW sensor.

Disc CD-3 effectuates a LAMP isothermal PCR detection methodology disclosed in the incorporated specification, where a fluid sample changes color based on the amount of DNA in the initial sample. In the illustrated embodiments no discs have detectors of more than one type, but the scope of the invention extends to the possibility that a disc having a combination of different types of detectors could be provided.

In the embodiment where the sample is a blood sample and the reader further includes a plasma-blood separating chamber having an inlet communicated to the sample inlet and an outlet for communicating plasma including the analyte from the first portion of the sample to the mixing chamber and from the second portion of the sample to the reaction chamber.

The detector includes a bar code reader for scanning of barcodes printed on disposable disk packages to collect information about the specific type of test being performed. Additionally, the barcode reader can read a barcode either on a smart device screen or patient wristband to identify and log the results corresponding to a specific patient.

The detector includes a TCP/IP Wi-Fi module for wirelessly transmitting information collected by the detector to a cloud infrastructure, and for receiving information transmitted by a cloud infrastructure, such as patient information, result analysis, and software updates The detector includes a Bluetooth module for both data transmission and remote control for wireless transmission of results and wireless operation of the detector.

The detector includes a capacitive touch screen for interacting with the detector and for displaying the results of the test to the user. The detector screen contains a graphical user interface, which includes the necessary steps to guide the user through the process of collecting a sample, inserting the microfluidic into the device, and displaying the final results of the test.

The detector includes a Peltier temperature control element which interfaces with the microfluidic disk for maintaining thermal equilibrium.

To resummarize, the illustrated embodiments of the invention include a method of diagnostically field testing a sample taken from a subject in a portable handheld instrument to determine the presence of viral antigens and/or antibodies thereto including the steps of: disposing the sample into a receiving chamber in a rotatable disc in the instrument; selectively processing the sample in the rotatable disc using the instrument according to the nature of the sample and the corresponding means of detection in the instrument of the viral antigens and/or antibodies subject to diagnostic testing; detecting a quantitative measure of the viral antigens and/or antibodies in the sample using the corresponding means of detection in the instrument; generating a data output of the detected quantitative measure of the viral antigens and/or antibodies in the sample corresponding to the subject; communicating the data output corresponding to the subject to a cloud-based database; comparatively analyzing in a cloud based ecosystem the communicated data output corresponding to the subject relative to a plurality of different types of viral antigens and/or antibodies to diagnose the type of viral infection, if any, the subject most likely carries or has previously carried; and communicating the results of the comparative analysis to the subject from the cloud-based ecosystem.

The means of detection comprises a microarray of antigen and/or antibody fluorescent spots. The step of detecting a quantitative measure of the viral antigens and/or antibodies in the sample using the corresponding means of detection in the instrument includes the step of generating an image file of a color image of the microarray of antigen and/or antibody fluorescent spots.

In another embodiment the means of detection comprises a functionalized surface acoustic wave detector (SAW). The step of detecting a quantitative measure of the viral antigens and/or antibodies in the sample using the corresponding means of detection in the instrument includes generating an RF phased delayed detection signal responsive to the quantification of viral antigens and/or antibodies directly captured by the functionalized surface acoustic wave detector (SAW) or indirectly captured polymerase chain reaction (PCR) replicated DNA tags by the functionalized surface acoustic wave detector (SAW) corresponding to viral antigens and/or antibodies.

The step of selectively processing the sample in the rotatable disc using the instrument according to the nature of the sample and the corresponding means of detection in the instrument of the viral antigens and/or antibodies subject to diagnostic testing includes the step of performing an ELISA blood test check for immunoglobulin G (IgG) and for Immunoglobin M (IgM) antibodies.

In another embodiment the step selectively processing the sample in the rotatable disc using the instrument according to the nature of the sample and the corresponding means of detection in the instrument of the viral antigens and/or antibodies subject to diagnostic testing includes the step of performing an immunofluorescence assay using a conjugated fluorescent label by direct or indirect immunofluorescence wherein the amount of conjugation of the antibody to the antigen is directly correlated with the amount of the fluorescence produced source.

In yet another embodiment the step of selectively processing the sample in the rotatable disc using the instrument according to the nature of the sample and the corresponding means of detection in the instrument of the viral antigens and/or antibodies subject to diagnostic testing includes the step of performing real time quantitative polymerase chain reaction (RT-qPCR) by rapid DNA amplification using PCR to measure the quantity of genetic material (DNA or RNA) in the sample and using Taq polymerase.

The step of selectively processing the sample in the rotatable disc using the instrument according to the nature of the sample and the corresponding means of detection in the instrument of the viral antigens and/or antibodies subject to diagnostic testing includes the steps of: capturing the analyte from a first portion of the sample with a first antibody having a DNA tag attached thereto and with a second antibody having an attached magnetic nanoparticle (MNP), where a sandwich is formed including the first and second antibodies, the analyte, the MNP and the DNA tag; and replicating the DNA tag using isothermal amplification to a predetermined amount of DNA tags sufficient to overcome the minimal mass sensitivity limitation of the detector by providing an amount is reliably detectable by a detector; disposing a second portion of the sample on a microarray; selectively probing the second portion of the sample for antibodies corresponding to the at least one selected virus using the microarray; and reading the microarray using a fluorescent camera to identify antibodies in the second portion of the sample.

In yet another embodiment the step of selectively probing the second portion of the sample for antibodies corresponding to the at least one selected virus using the microarray includes the steps of: incubating the second portion of the sample on the microarray for a predetermined amount of time; disposing fluorescence labelled secondary Ab; washing the microarray; and drying the microarray. The step of reading the microarray using a fluorescent camera to identify antibodies in the second portion of the sample includes the steps of: detecting Ig isotypes in the second portion of the sample by generating a color image of the microarray; and communicating the color image of the microarray to the cloud for analysis and/or data processing.

In one embodiment the microarray has been provided with DNA spots of receptor binding domain (ROD) of spike protein, and the step of selectively probing the second portion of the sample for antibodies corresponding to the at least one selected virus using the microarray includes the steps of: performing a neutralizing antibody assay using the microarray provided with DNA spots of receptor binding domain (RBD) of spike protein and fluorophore labelled ACE2 and another fluorophore labelled secondary antibody against human IgG for detection of RBD antibody; washing the microarray; and drying the microarray. The step of reading the microarray using a fluorescent camera to identify antibodies in the second portion of the sample includes the steps of generating a color image of the microarray with at least two different colors, one color for RBD antibody present in the second portion of the sample and a second color for ACE2, the second portion of the sample without neutralizing antibodies or RBD antibodies being detected with ACE2 fluorescence, while samples with RBD antibodies or increasing amount of neutralizing antibodies that interfere with ACE2-RBD binding being detected with a decreasing amount of ACE2 fluorescence, where In the absence of RBD antibodies, the amount of ACE2 fluorescence can be quantified for relative neutralizing activity; and communicating the color image of the microarray to the cloud for analysis and/or data processing.

The step of selectively probing the second portion of the sample for antibodies corresponding to the at least one selected virus using the microarray further includes the steps of micro-mixing the second portion of the sample using reciprocation in which centrifugal acceleration acting on a liquid element first generates and stores pneumatic energy that is then released by a reduction of the centrifugal acceleration, resulting in a reversal of direction of flow of the liquid, and applying an alternating sequence of high and low centrifugal acceleration to the second portion of the sample to maximize incubation/hybridization efficiency between antibodies and antigen macromolecules during the incubation/hybridization.

The step of comparatively analyzing in a cloud based ecosystem the communicated data output corresponding to the subject relative to a plurality of different types of viral antigens and/or antibodies to diagnose the type of viral infection, if any, the subject most likely carries or has previously carried includes the steps of: analyzing the communicated data output of an microarray for positive and/or negative indications of Covid-19 antigens and/or antibodies; comparing the communicated data output for positive and/or negative indications of Covid-19 to communicated data output for positive and/or negative indications of the microarray for a plurality of viral infections sharing at least some of the Covid-19 antigens and/or antibodies; and determining whether the communicated data output of positive and/or negative indications are statistically indicative of Covid-19 rather than the plurality of viral infections sharing at least some of the Covid-19 antigens and/or antibodies, so that false positives and/or false negatives are substantially reduced.

The step of determining whether the communicated data output of positive and/or negative indications are statistically indicative of Covid-19 rather than the plurality of viral infections sharing at least some of the Covid-19 antigens and/or antibodies includes the step of determining whether the corresponding Z-scores of the communicated data output of positive and/or negative indications are indicative of Covid-19 rather than the Z-scores of the plurality of viral infections sharing at least some of the Covid-19 antigens and/or antibodies The step of comparing the communicated data output for positive and/or negative indications of Covid-19 to communicated data output for positive and/or negative indications of the microarray for a plurality of viral infections sharing at least some of the Covid-19 antigens and/or antibodies includes the step of comparing the communicated data output for positive and/or negative indications of Covid-19 to communicated data output for positive and/or negative indications of the microarray for a plurality of acute respiratory infections selected from the group including SARS-CoV-2, SARS-CoV, MERS-CoV, common cold coronaviruses (HKU1, OC43, NL63, 229E), and multiple subtypes of influenza, adenovirus, metapneumovirus, parainfluenza, and/or respiratory syncytial virus.

The step of determining whether the communicated data output of positive and/or negative indications are statistically indicative of Covid-19 rather than the plurality of viral infections sharing at least some of the Covid-19 antigens and/or antibodies, so that false positives and/or false negatives are substantially reduced includes the step of evaluating antigens to discriminate output data of a positive group of antigens from a negative group antigens across a range of assay cutoff values using receiver-operating-characteristic (ROC) curves for which an area-under curve (AUC) is measured to determine high performing antigens to diagnose Covid-19.

The step of determining whether the communicated data output of positive and/or negative indications are statistically indicative of Covid-19 rather than the plurality of viral infections sharing at least some of the Covid-19 antigens and/or antibodies, so that false positives and/or false negatives are substantially reduced includes the step of determining an optimal sensitivity and specificity for Covid-19 from a combination of a plurality of high-performing antigens based on a corresponding Youden index calculated for the combination of plurality of high-performing antigens.

The scope of the illustrated embodiments of the invention also extend to a portable, handheld microfluidic reader for assaying an analyte in a sample, the reader having a rotatable microfluidic disc. The reader includes: a sample inlet defined in the disc into which the sample is disposed; a mixing chamber defined in the disc and selectively communicated to the sample inlet and provided with a first antibody for capturing the analyte having a DNA tag attached thereto; an amplification chamber defined in the disc selectively communicated to the mixing chamber provided with a second antibody for capturing the analyte attached to a surface or having a magnetic nanoparticle (MNP) attached thereto, where a sandwich including the surface or MNP, first and second antibodies, the analyte and the DNA tag is formed in the amplification chamber; and for replicating the DNA tag using isothermal amplification to produce a predetermined amount of DNA tags; a detector selectively communicated to the amplification chamber and provided in the disc for measuring the amount of replicated DNA tags; a reaction chamber for receiving a second portion of the sample; a microarray disposed in the reaction chamber for selectively probing the second portion of the sample for antibodies corresponding to the at least one selected virus using the microarray; and a fluorescence camera for reading the microarray to identify antibodies in the second portion of the sample.

In one embodiment the detector is a surface wave acoustic (SAW) detector.

In one embodiment the sample is a blood sample and the reader includes a plasma-blood separating chamber having an inlet communicated to the sample inlet and an outlet for communicating plasma including the analyte from the first portion of the sample to the mixing chamber and from the second portion of the sample to the reaction chamber.

The illustrated embodiments also can be characterized as a portable, handheld microfluidic reader for assaying an analyte in a sample and for operating in a cloud ecosystem. The reader has a rotatable microfluidic disc and includes: a fluidic circuit in the disc into which fluidic circuit the sample is disposed and processed; a microarray having a plurality of fluorescently tagged antigen and/or antibody probes disposed in the fluidic circuit for selectively probing the sample for antibodies and/or antigens corresponding to the at least one selected virus; a fluorescence color camera for imaging the microarray to identify antibodies and/or antigens in the sample; and a circuit for generating output data corresponding to the image of the microarray to quantify the amount of probed and detected antigens and/or antibodies in the sample and to communicate the output data to the cloud ecosystem.

The portable, handheld microfluidic reader further includes in combination a cloud-based database and processor for receiving the output data from the reader and statistically diagnosing a present viral infection or evidence of past viral infection from the probed and detected antigens and/or antibodies in the sample.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1a is a fluorescence spectrograph segments corresponding to a plurality of viruses, shown side by side. FIG. 1b is an enlargement of Covid 19, SARS-Cov and MERS-Covid portions of the spectra.

FIG. 6 is a diagram illustrating the method of antiviral Ab detection in blood using antigen array or viral antigen detection in nasal secretions on antibody array.

FIG. 7 is a diagram of a method for using an antibody neutralizing assay using array of RBD antigen.

Figure 10A:
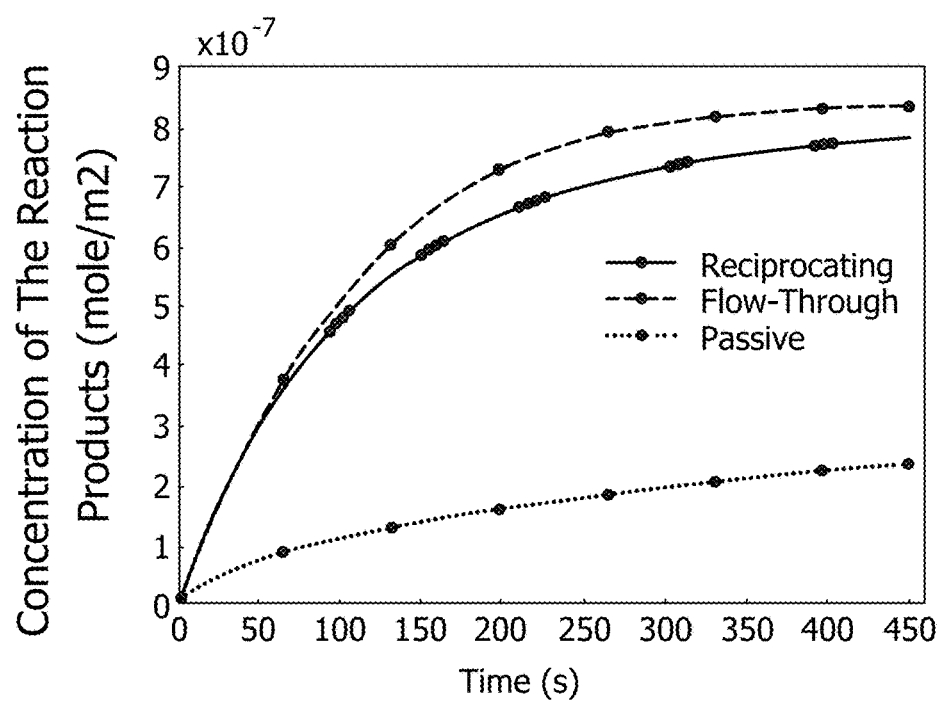
Figure 10B:
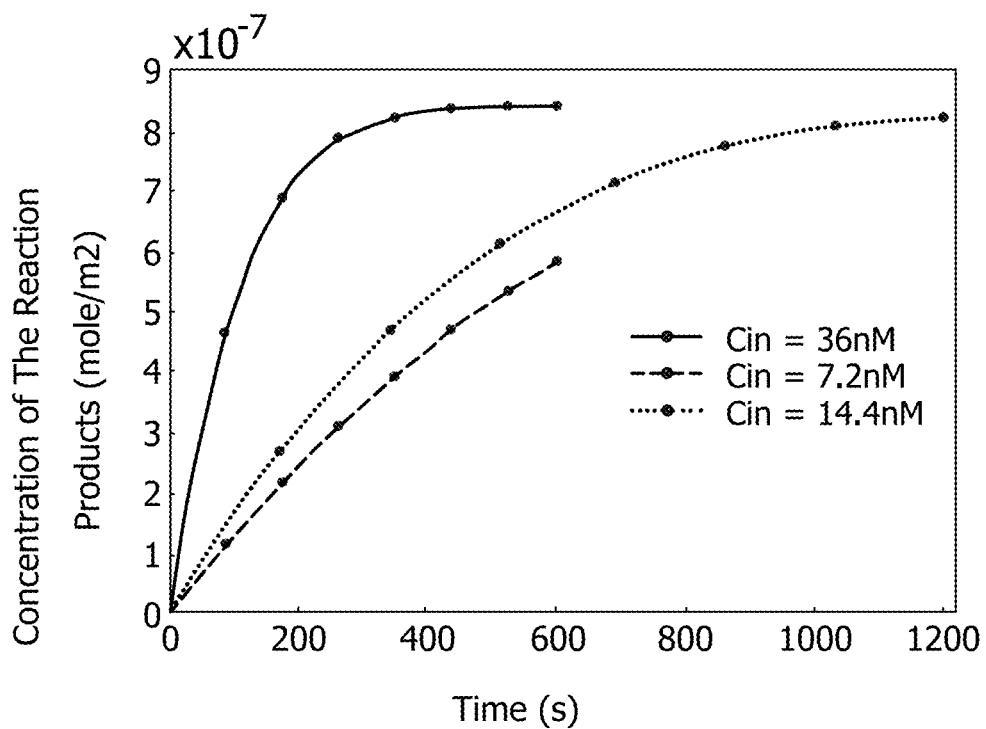
Figure 10C:
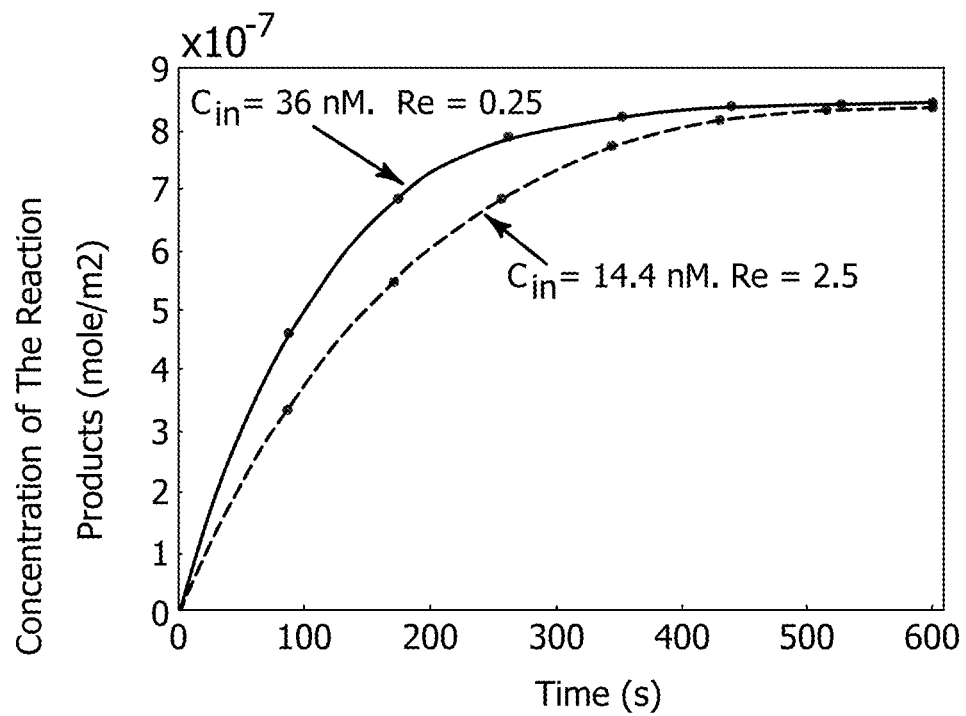

The graphs of FIGS. 10a-10c compares the characteristics of reciprocating flow used in the illustrated embodiments for incubation relative to single flow and passive diffusion.

Figure 11:
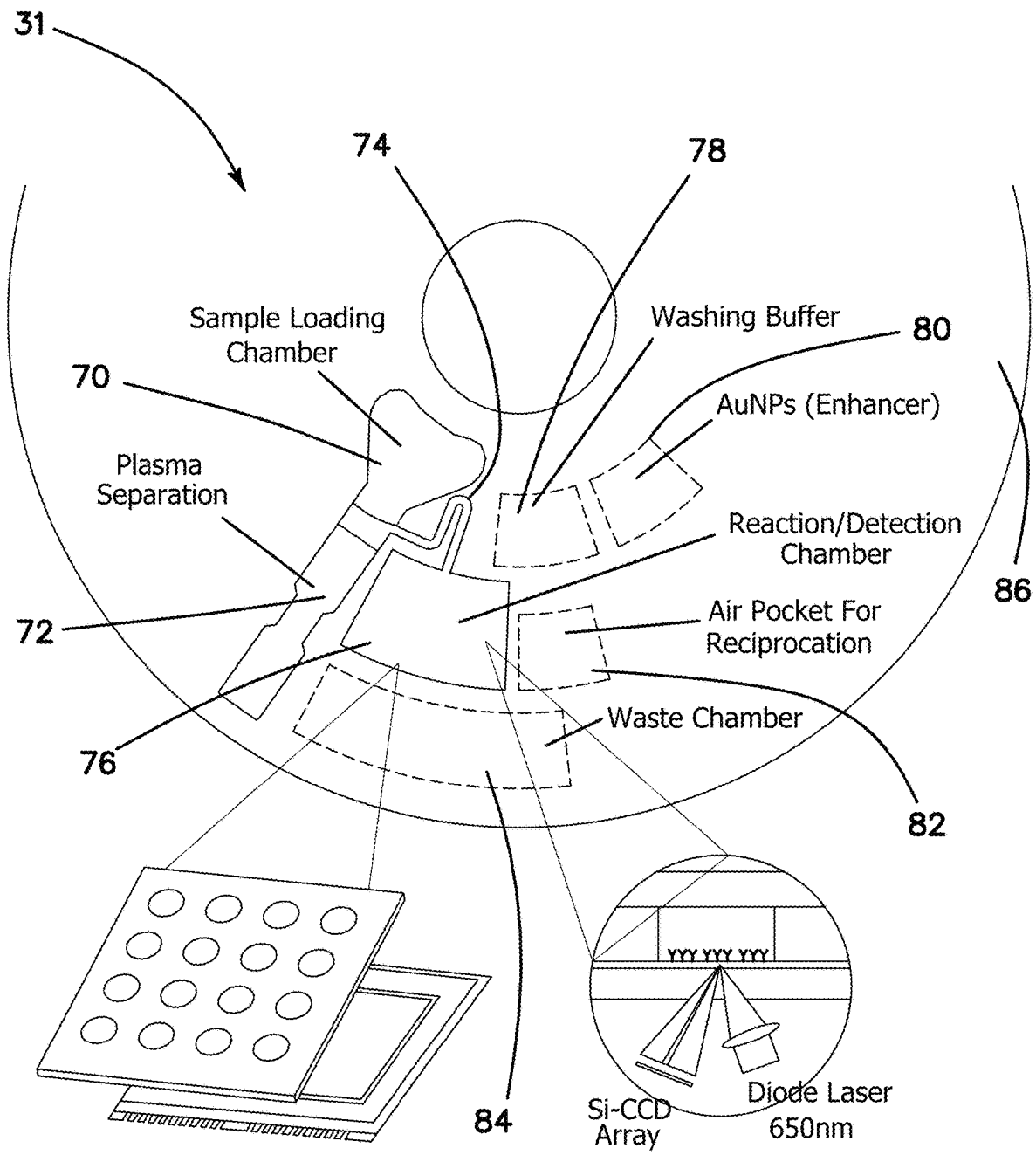

FIG. 11 is a diagram of the fluorescence biosensor of the illustrated embodiments of a protein array with a CMOS laser/diode chip below for signal readout in a disc CD-1.

Figure 12:
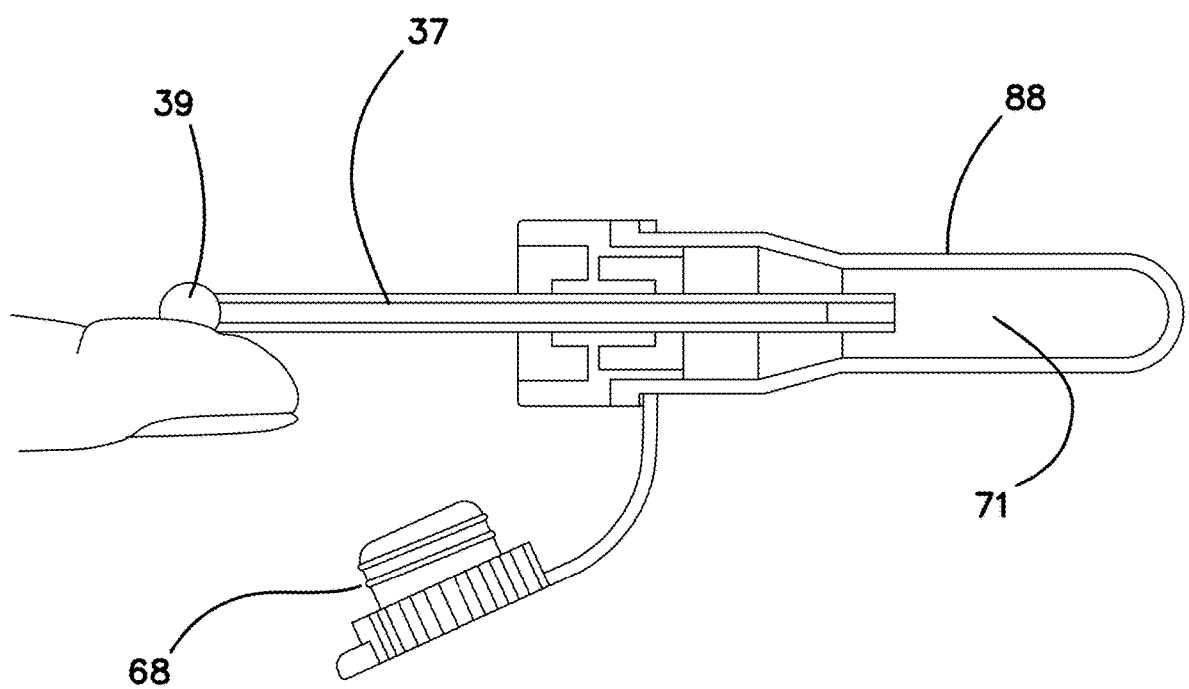

FIG. 12 is a diagram illustrating a microlancet and 300 µL microvette into which a blood sample is drawn.

FIGS. 13a-13f are cross sectional views of cone that can accept a nasal swab, cut it, resuspend with buffer and lysis beads, release reagents, perform cell lysis, and evacuate sample onto the disc.

Figure 14:
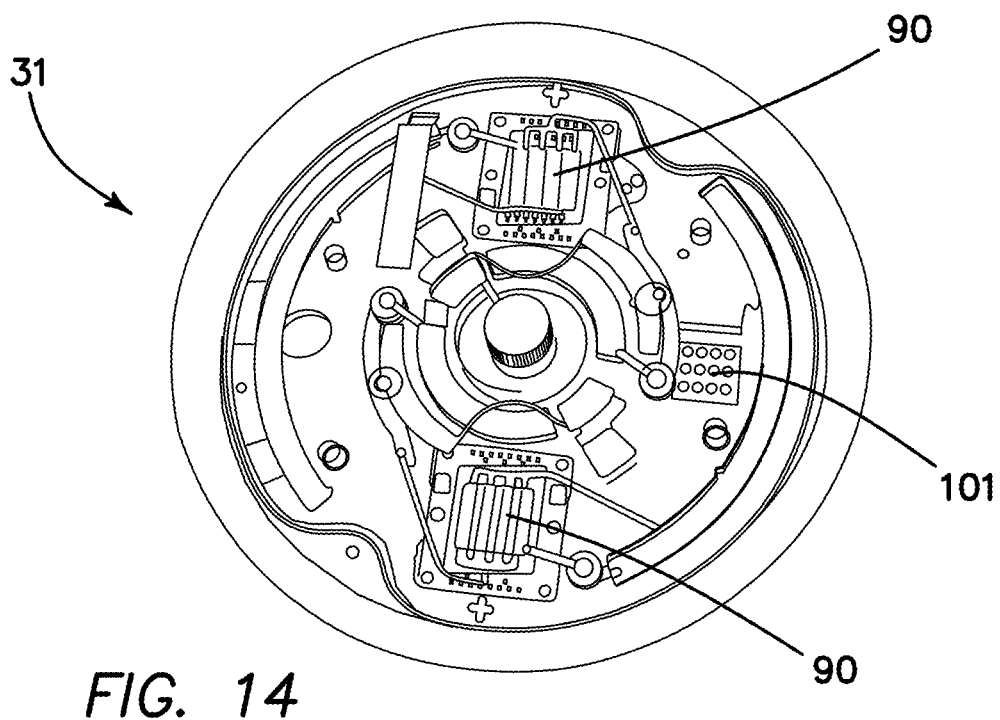

FIG. 14 is a diagram of a CD rotor including two SAW detectors, corresponding fluidic circuits and RF interposer in disc CD-2.

Figure 15:
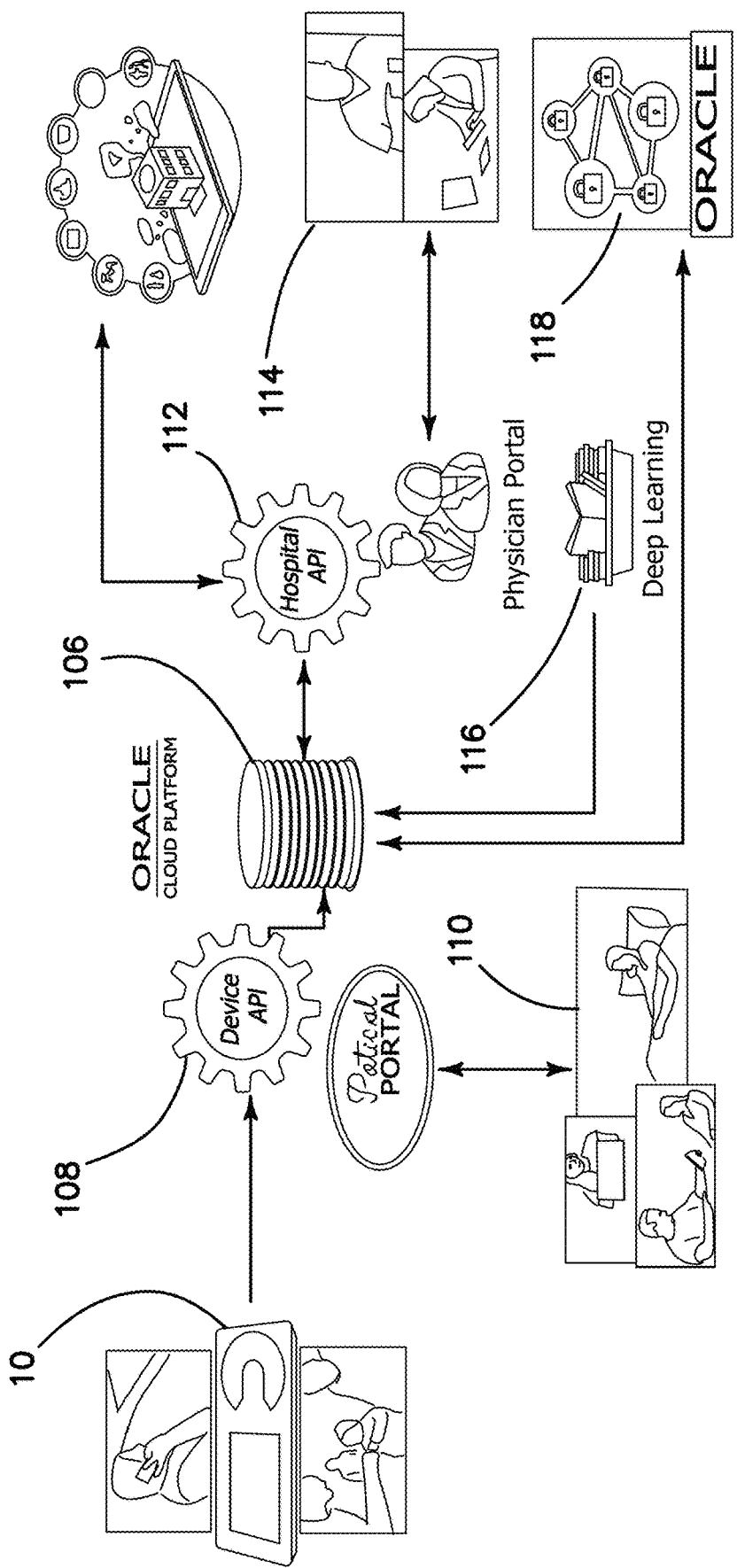

FIG. 15 is a diagram of the Optikus II could infrastructure.

Figure 16:
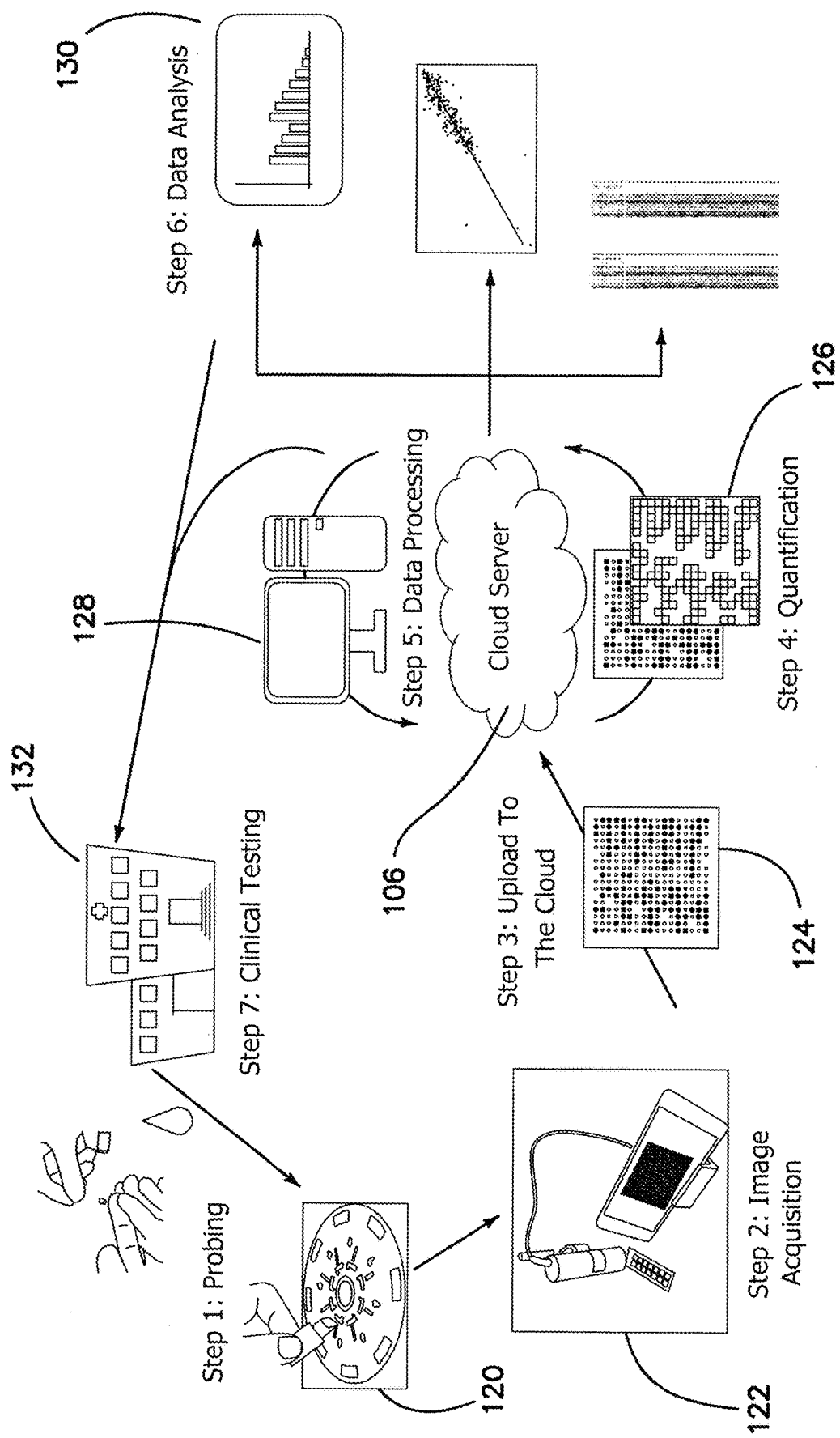

FIG. 16 is a diagram illustrated a method of use of Optikus II using a cloud infrastructure.

Figure 17:
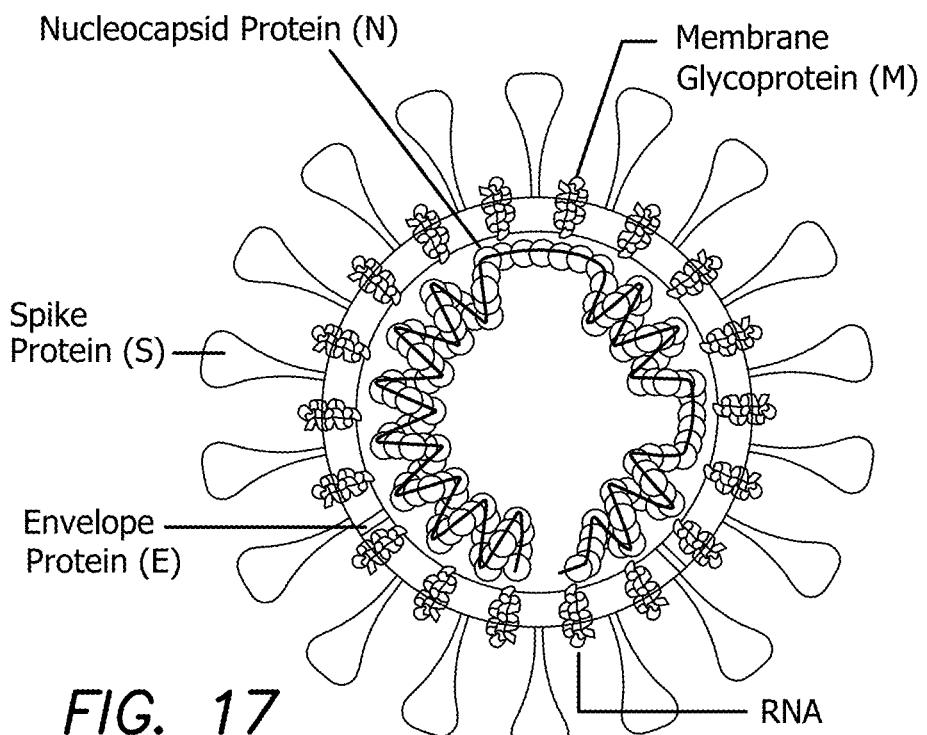

FIG. 17 is a diagram of the structure of the novel corona virus.

FIGS. 18a-18d are graphs of an individual patient's fluorescent scores for IgG and IgM detection in a sample using a microarray, and the corresponding Z-score statistics. The red line is an average positive result used to assess whether a measure is positive. The blue line is an average of negative results. The red corresponds to an average seropositive result which is additionally confirmed via PCR. The blue line corresponds to an average seronegative result which is confirmed via PCR. If a patient's IgG bar graph looks like the red line, they test positive, if it looks like the blue line they test negative.

Figure 18A:
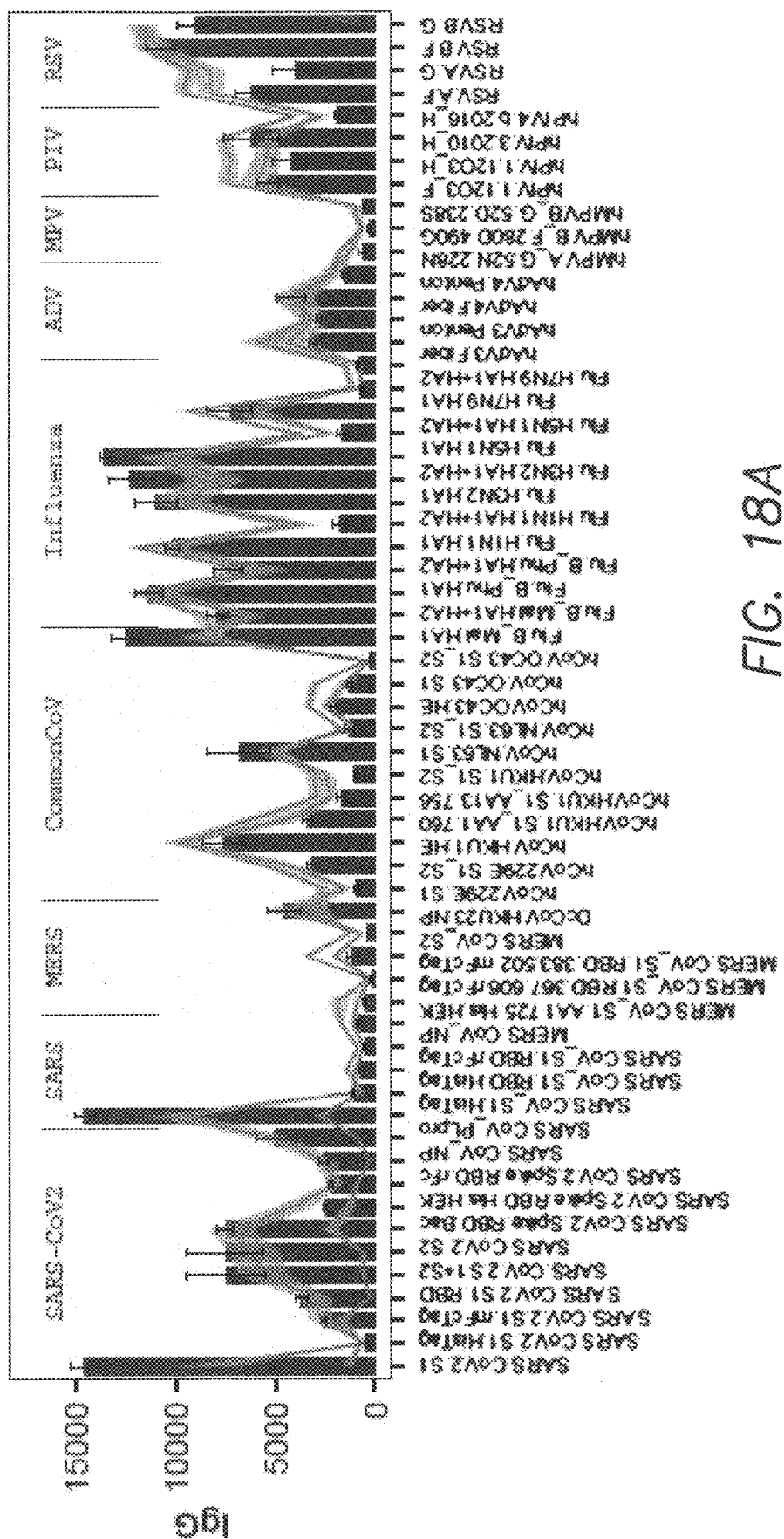
Figure 18B:
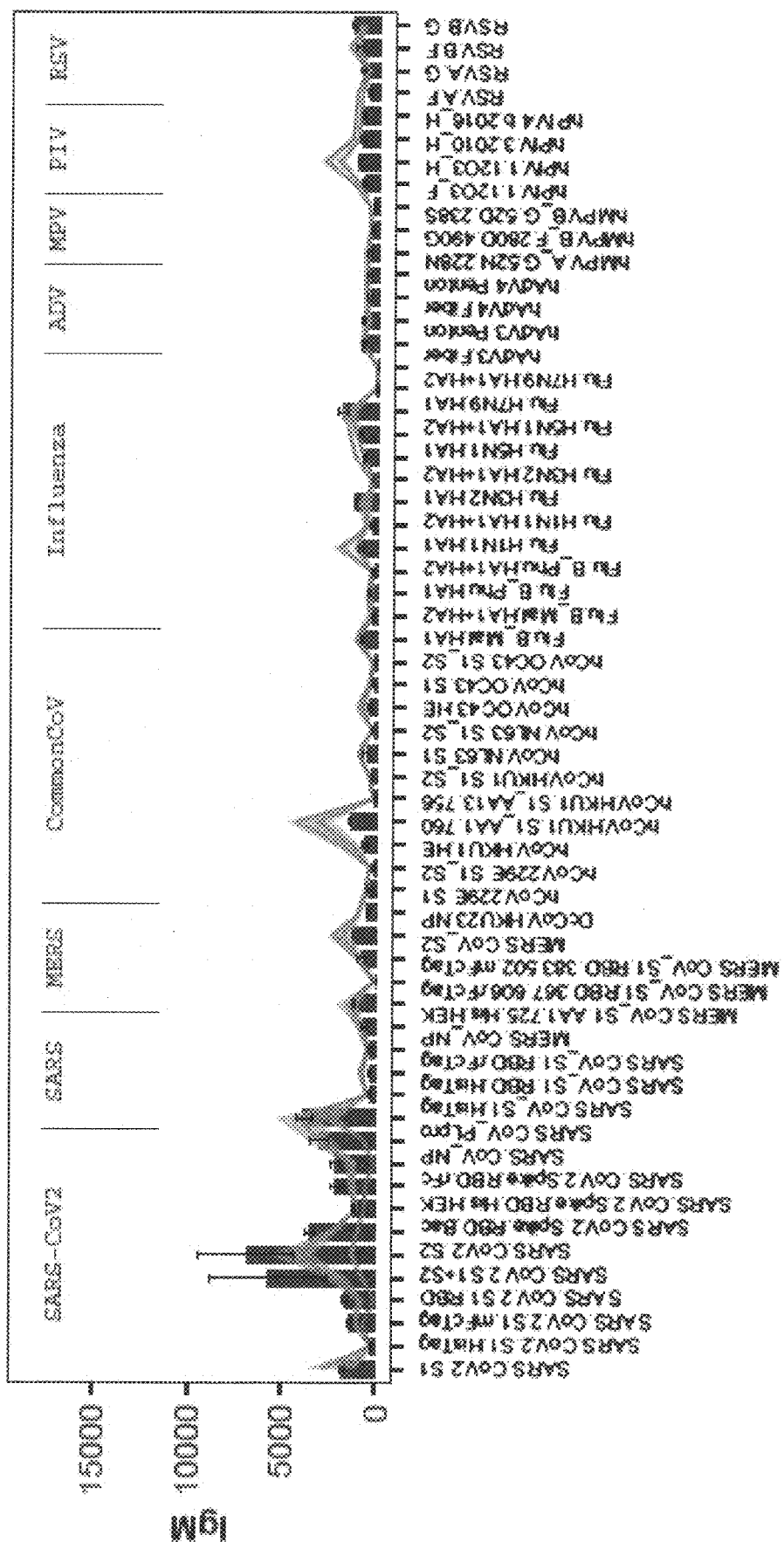
Figure 18C:
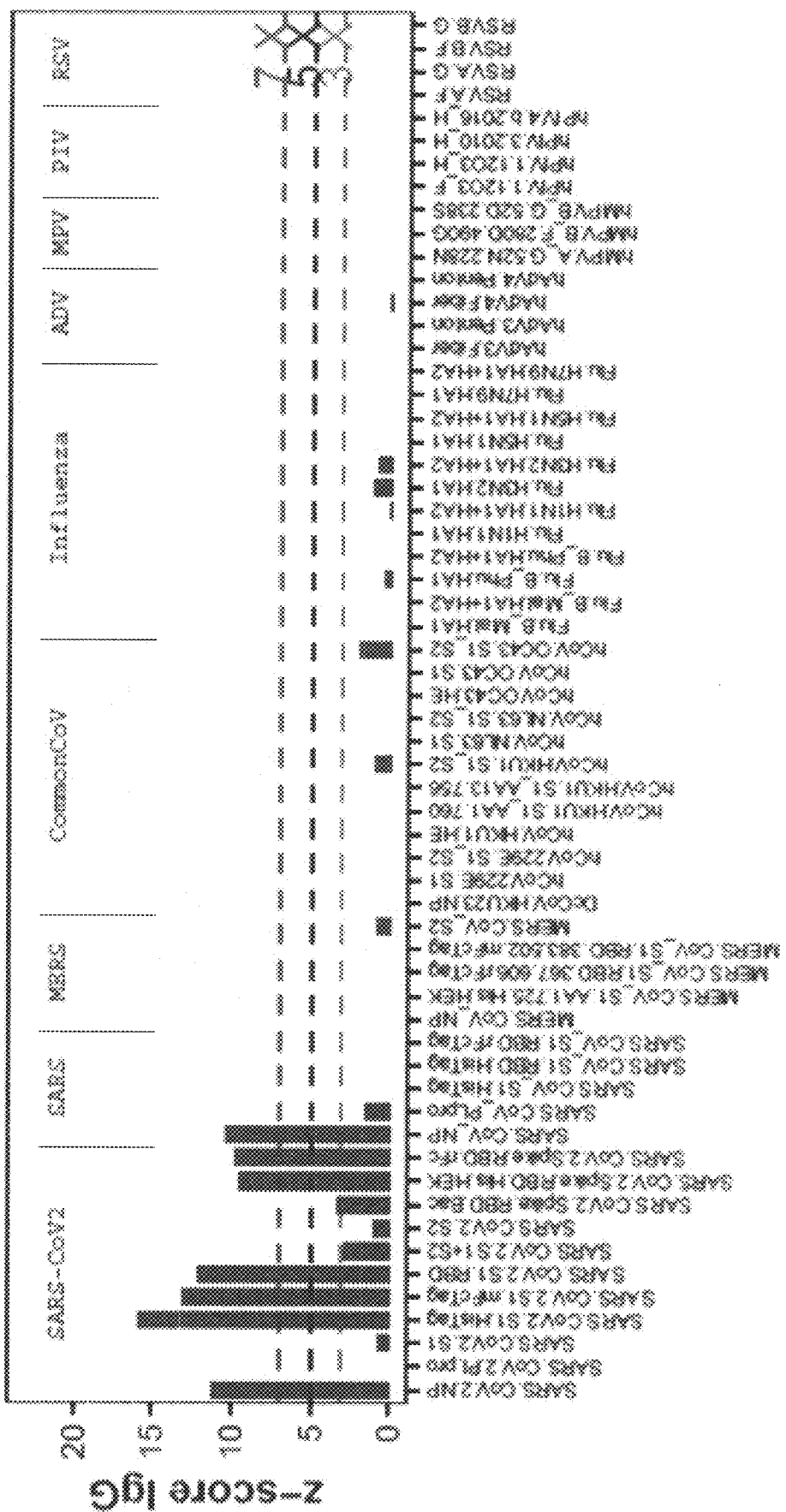

FIG. 18a is a graph of the fluorescent scores for IgG for several viruses, namely SARS-CoV2, SARS, MERS, CommonCoV, Influenza, ADV, MPV, PIV and RSV as a function of the DNA dots on the microarray as seen as listed on the x-axis in FIG. 18c.

Figure 18D:
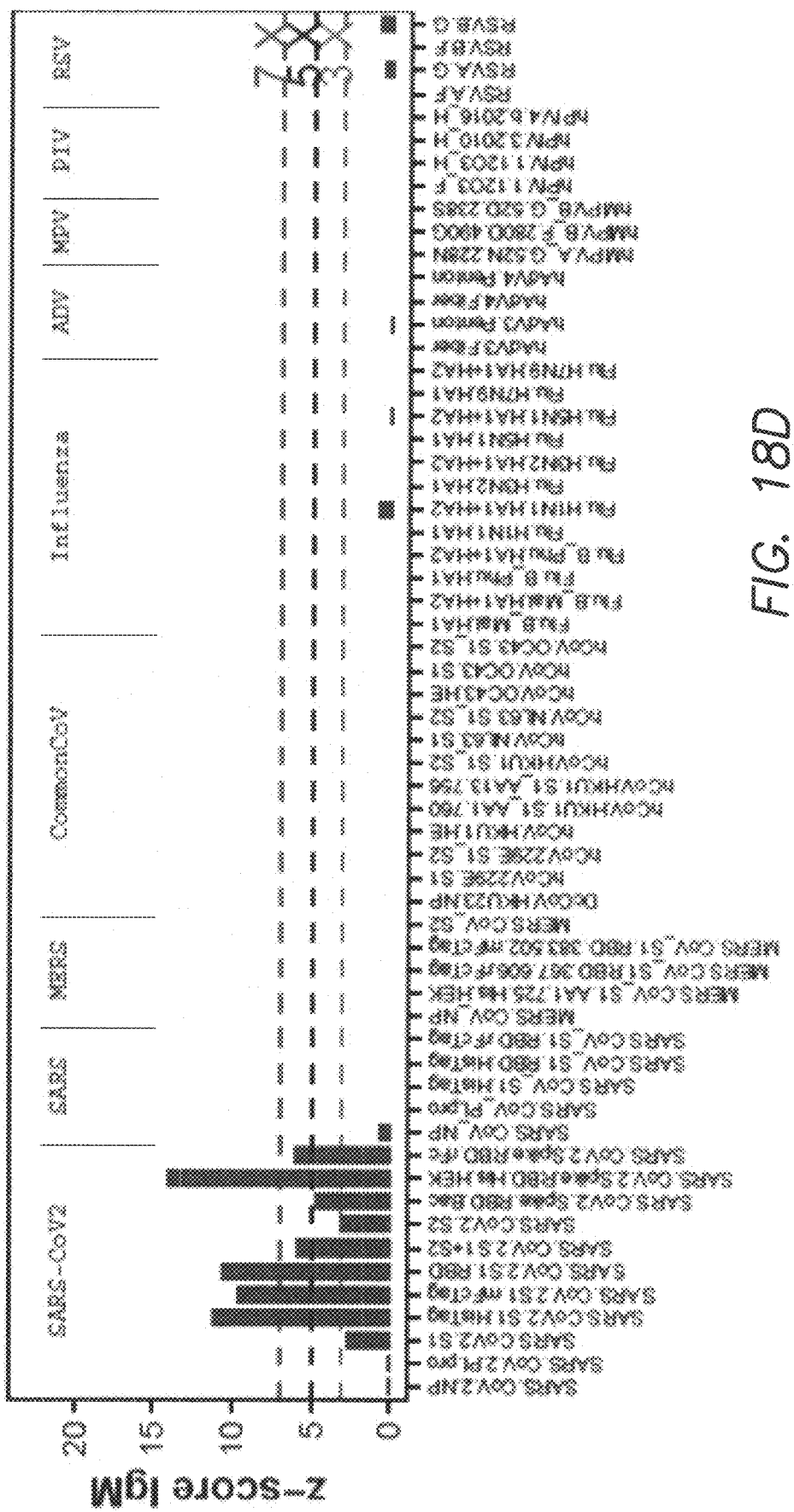

FIG. 18b is a graph of the fluorescent scores for IgM for several viruses, namely SARS-CoV2, SARS, MERS, CommonCoV, Influenza, ADV, MPV, PIV and RSV as a function of the DNA dots on the microarray as seen as listed on the x-axis in FIG. 18d.

FIG. 18c is a bar graph of the Z-score statistics of the IgG readings for several viruses, namely SARS-CoV2, SARS, MERS, CommonCoV, Influenza, ADV, MPV, PIV and RSV as a function of the DNA dots on the microarray as listed on the x-axis.

FIG. 18d is a bar graph of the Z-score statistics of the IgM readings for several viruses, namely SARS-CoV2, SARS, MERS, CommonCoV, Influenza, ADV, MPV, PIV and RSV as a function of the DNA dots on the microarray as listed on the x-axis.

Figure 19:
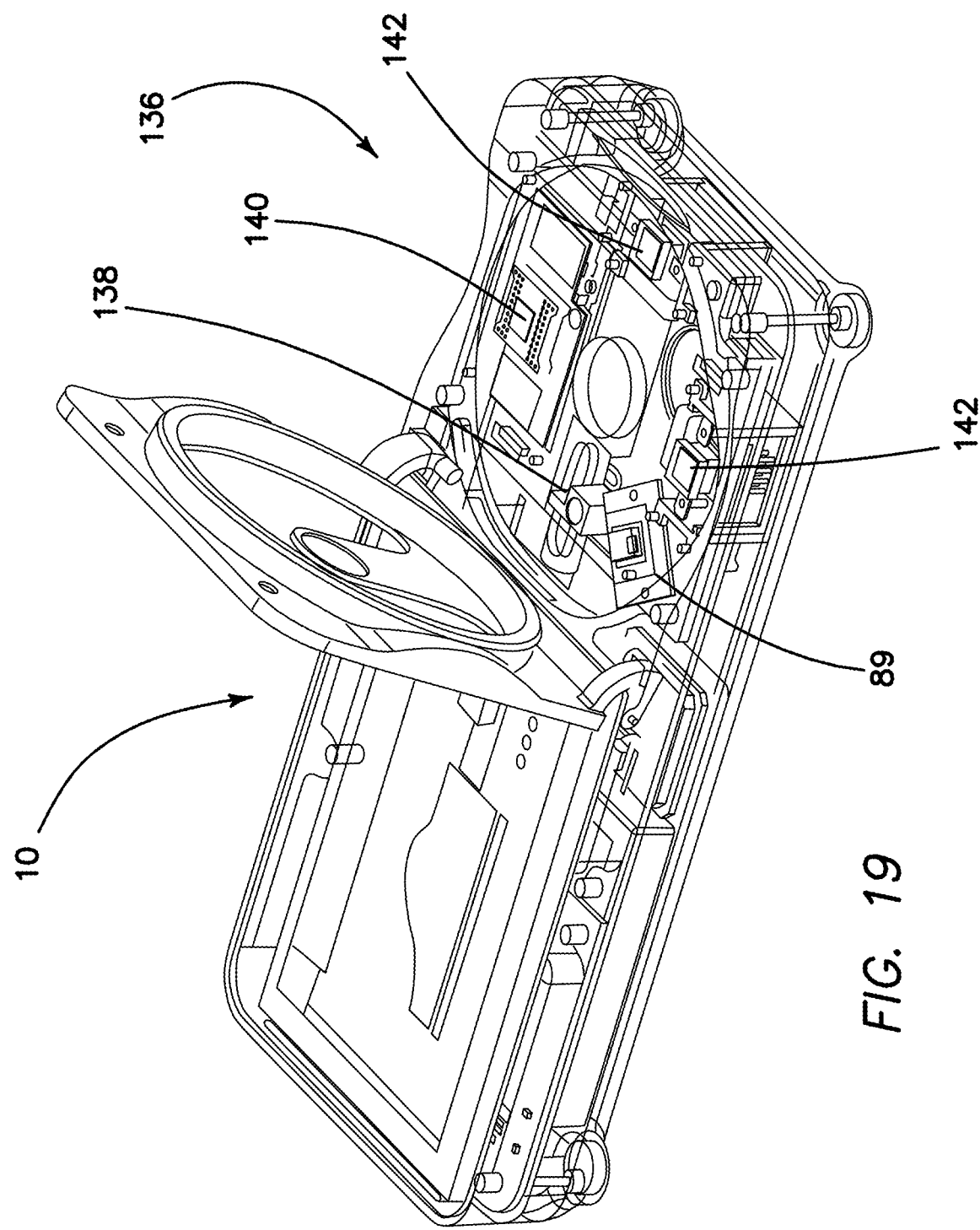

FIG. 19 is a top perspective transparent view of the Optikus reader with the microfluidic bay exposed.

Figure 20A:
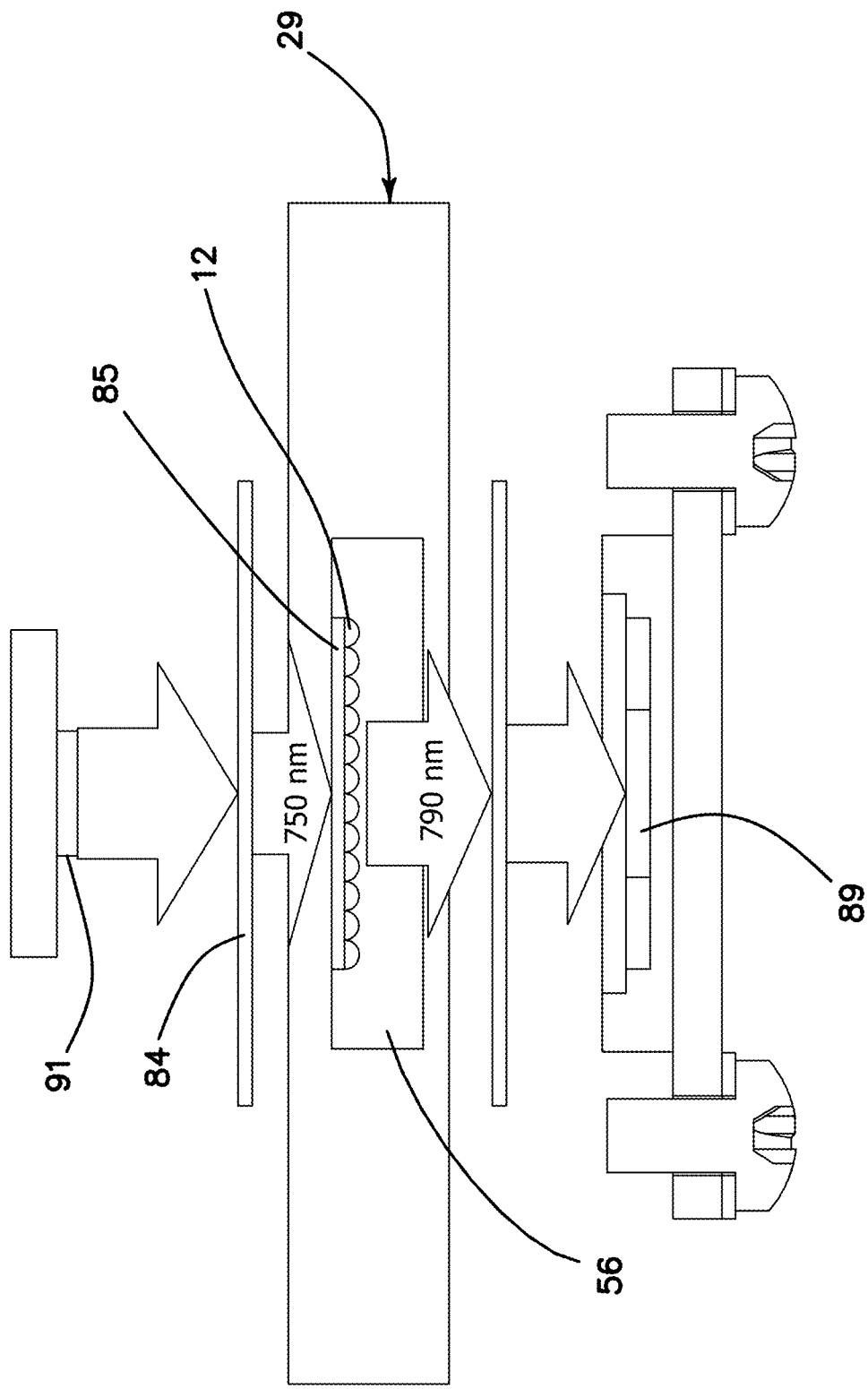
Figure 20B:
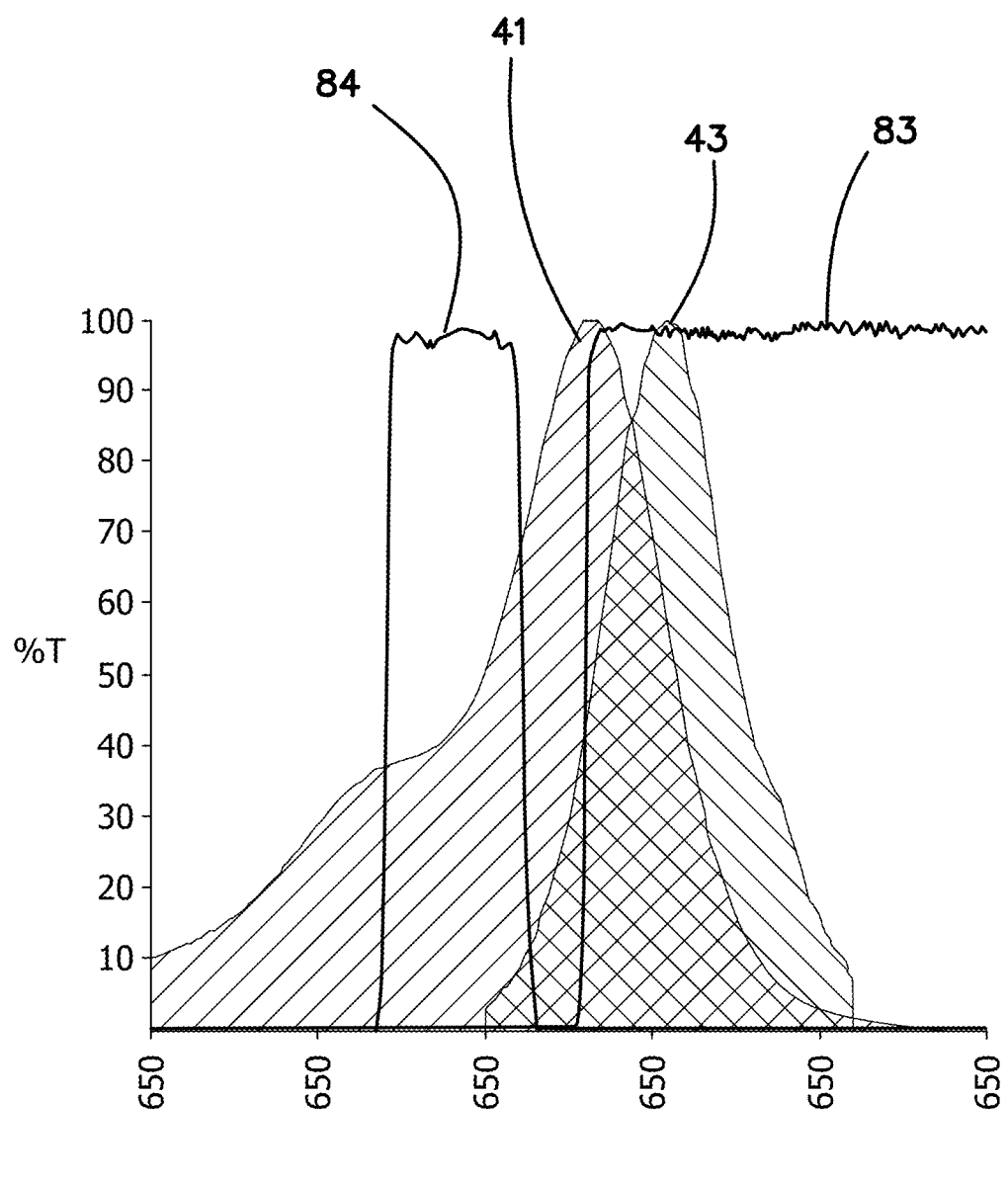

FIG. 20a is a diagram of a sideview of the LED excitation of the microarray assay and detection by the CMOS camera. FIG. 20b is a transmission spectrograph of the excitation spectrum and emission spectrum of a sample with the LED emission filter and camera notch filter spectrum overlaid.

Figure 21:
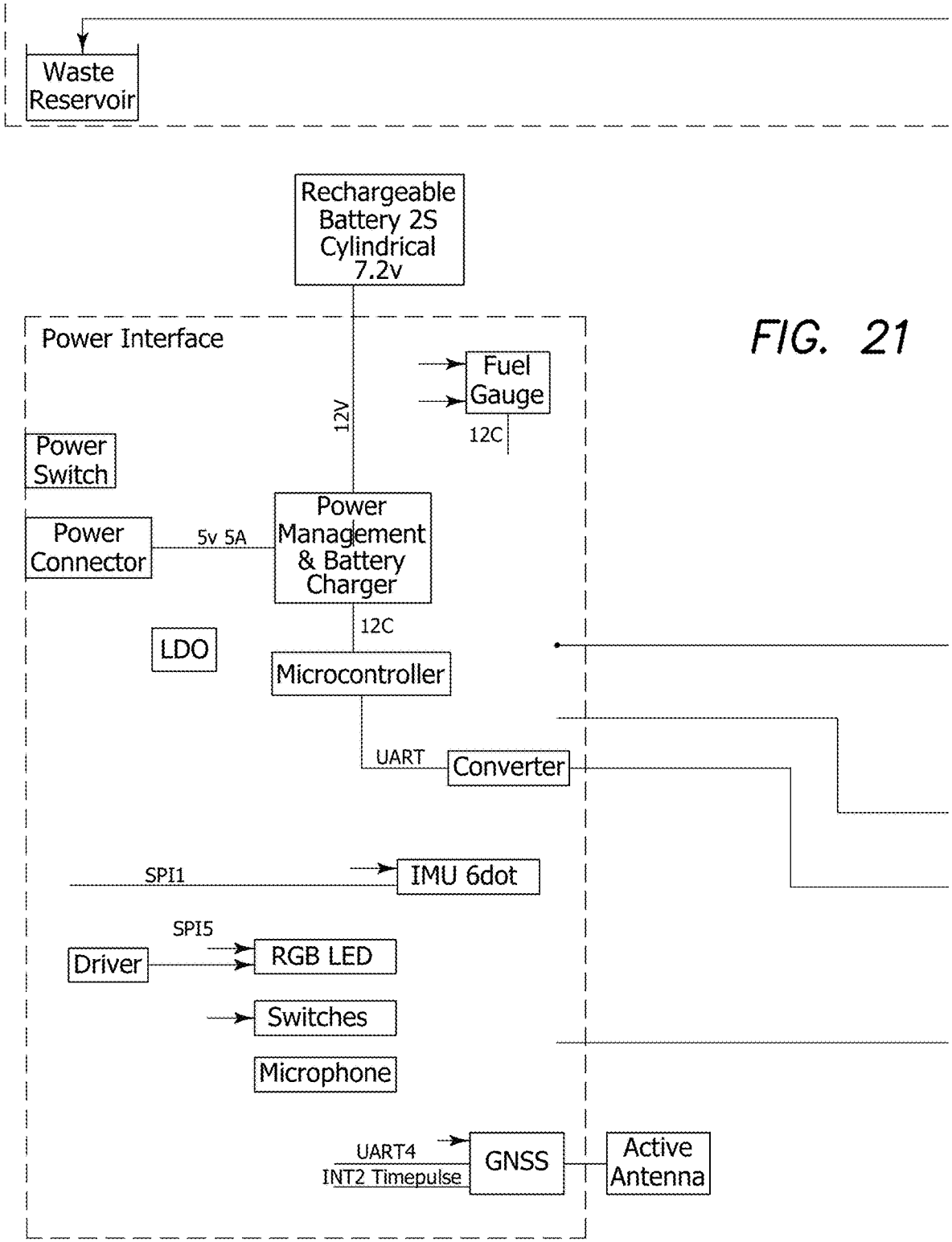
Figure 21:
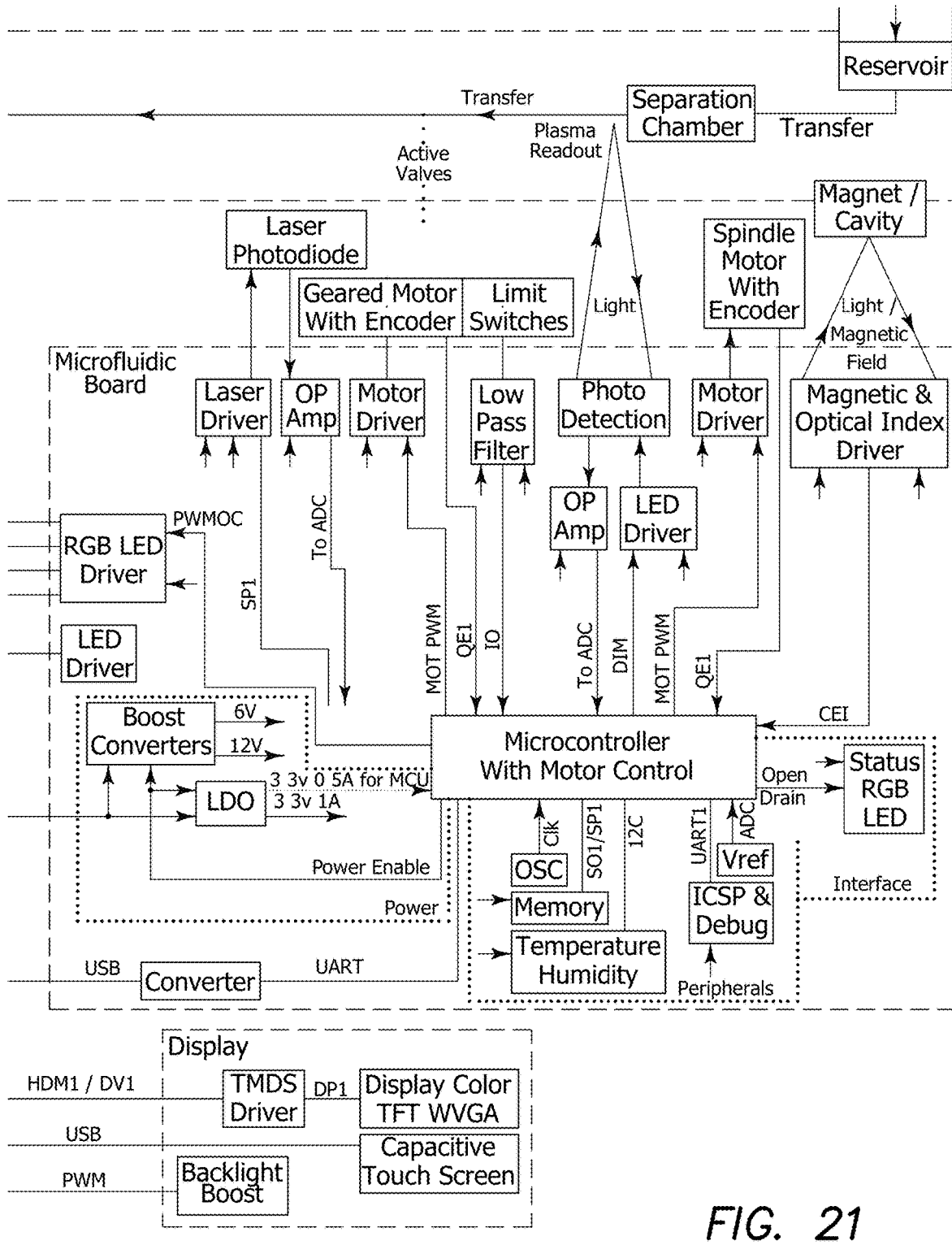

FIG. 21 is a block diagram of the electronic components in the Optikus used for microarray measurements.

Figure 22:
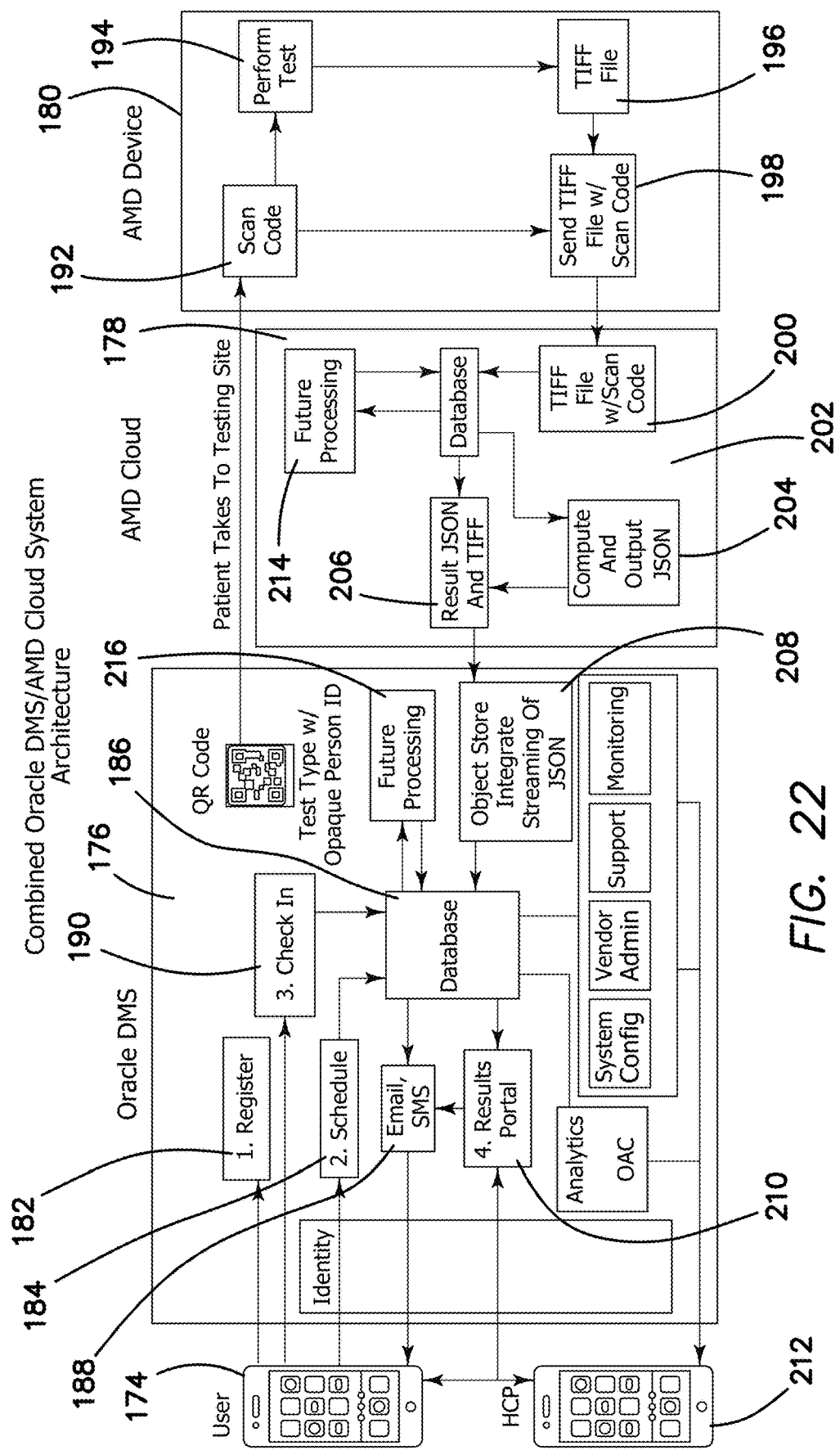

FIG. 22 is a block diagram of an example use of a cloud ecosystem to interface with the device, receive data, compute results, and return the results to the device.

Figure 23:
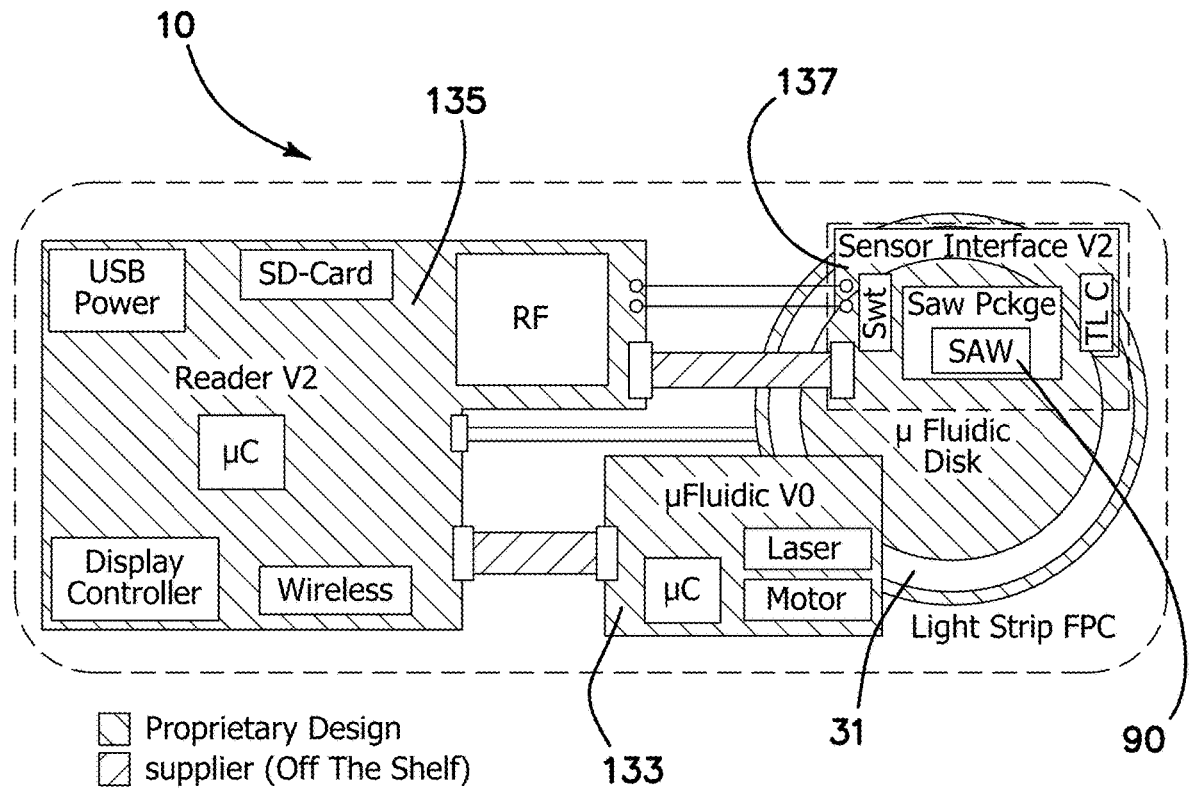

FIG. 23 is a block diagram of the instrument having a SAW sensor as the detector.

Figure 24:
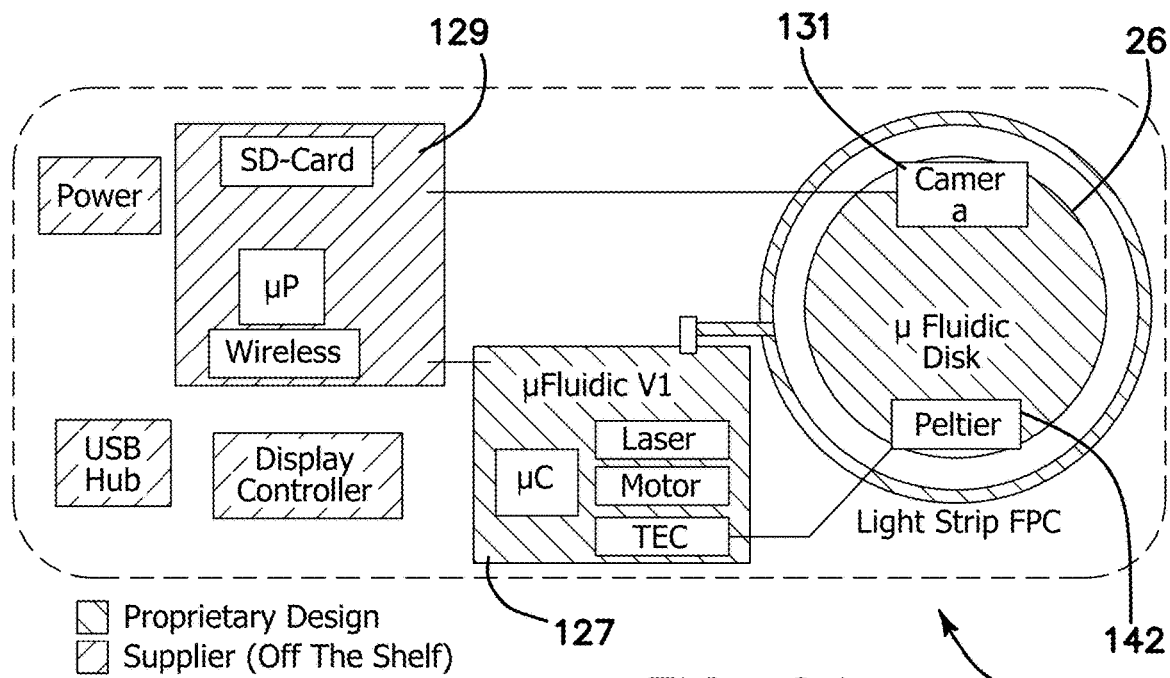

FIG. 24 is a block diagram of the instrument having an optical sensor as the detector.

Figure 25:
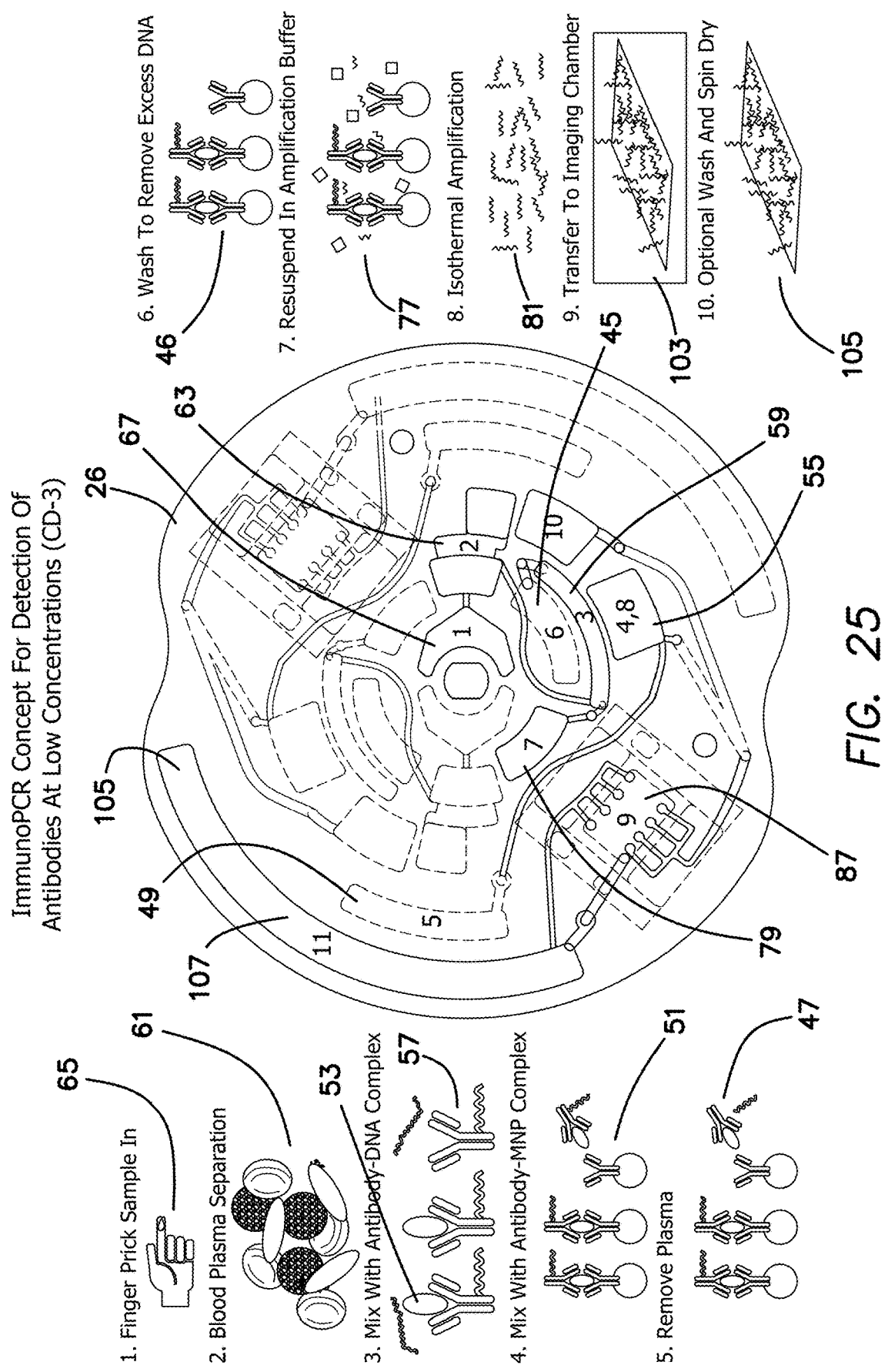

FIG. 25 is a diagram of a disc CD-3 used for immunoPCR illustrating the sequence of steps carried out on the disc.

Figure 1A:
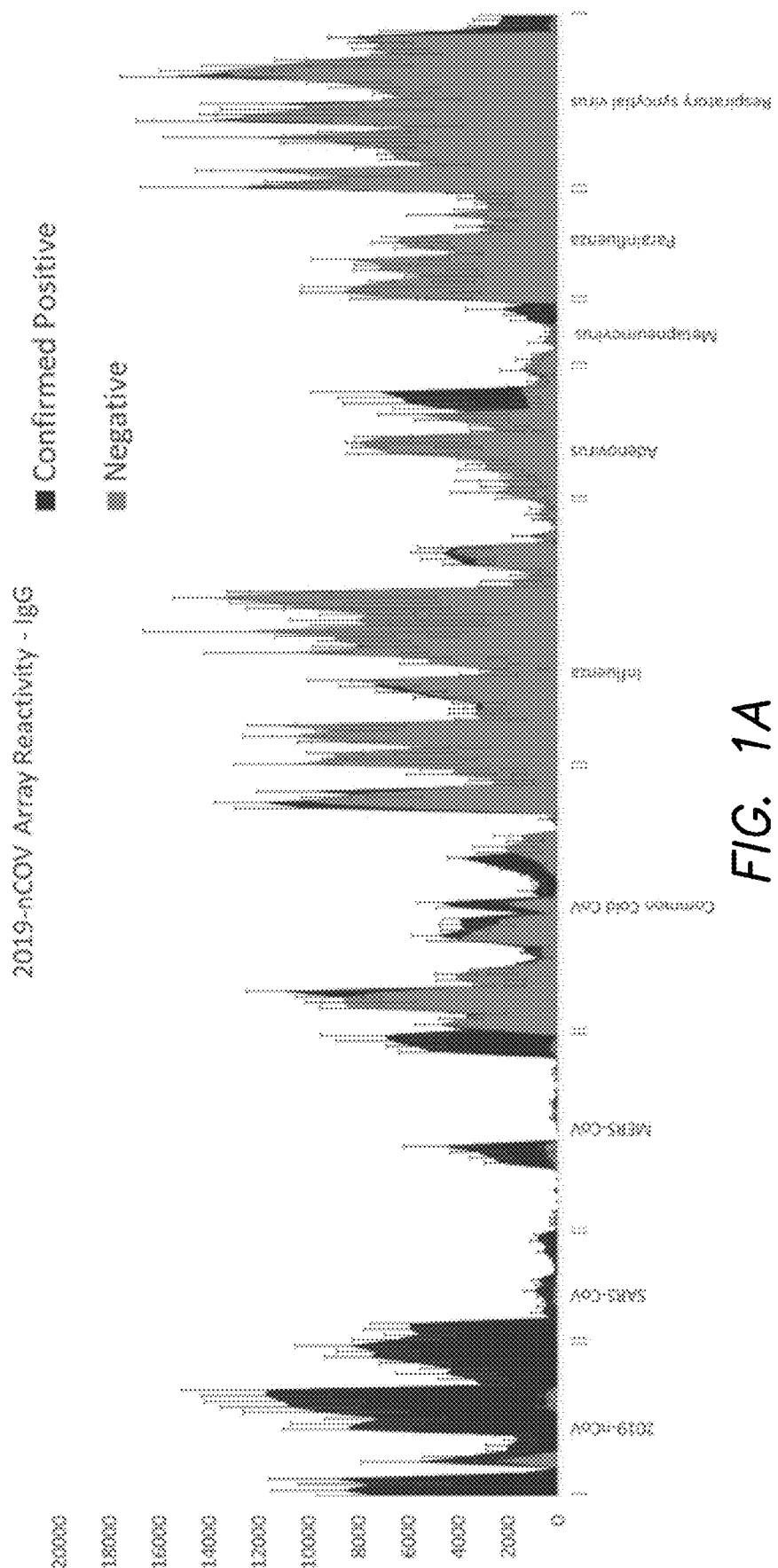
FIGS. 1a and 1b are graphs showing the IgG seroreactivity as measured by means of the fluorescence intensity of serum specimens on the coronavirus antigen microarray vs frequency. This array is embedded in disc CD-1 for the Optikus platform.

FIG. 26 is a table showing the fluorescent intensity results for IgG shown in FIG. 18a, the Z-score statistics for the fluorescent results in FIG. 18c, the fluorescent intensity results for IgM shown in FIG. 18b, and the Z-score statistics for the fluorescent results of FIG. 1d.

FIG. 27 is a table showing the performance data for combinations of high-performing antigens.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Over the past decades, rising numbers of emerging infectious diseases have caused serious societal and economic impact worldwide. In particular, rural third-world communities experience high exposure to infectious diseases, but also face numerous challenges in healthcare access. Nevertheless, pathogens do not know country boundaries and new disease outbreaks anywhere affect people everywhere. Expert-curated knowledge, software and services to support the interpretation of medical diagnostic test results from a world-wide interconnected point-of-care (POC) network that tracks and prevents fast spreading infectious disease pandemics is the only way mankind can expect to maintain vibrant economies and highly mobile societies.

The disclosed approach of the illustrated embodiments overcomes the problems associated with currently available COVID-19 diagnostic equipment by first measuring both pathogen directly and pathogen antibodies. The SKC-Optikus-2020 executes all three types of measurements listed above. The different types of tests require a different type of disposable cartridge in the shape of a compact or microfluidic disk (CD), namely a disc 29, CD-1, for ELISA, a disc 31, CD-2, for Immunofluorescence or SAW detection and a disc 26, CD-3, for RT-qPCR). The protein array on disc 29 CD-1 can be carried out in less than 10 minutes. The direct virus test on disc 31, CD-2 takes less than 12 minutes. The antibody test on disc 29 CD-1 is carried out first and when pathogen antibodies are discovered the associated pathogen test is then performed (either using disc 31 CD-2 or disc 26 CD-3).

Figure 1B:
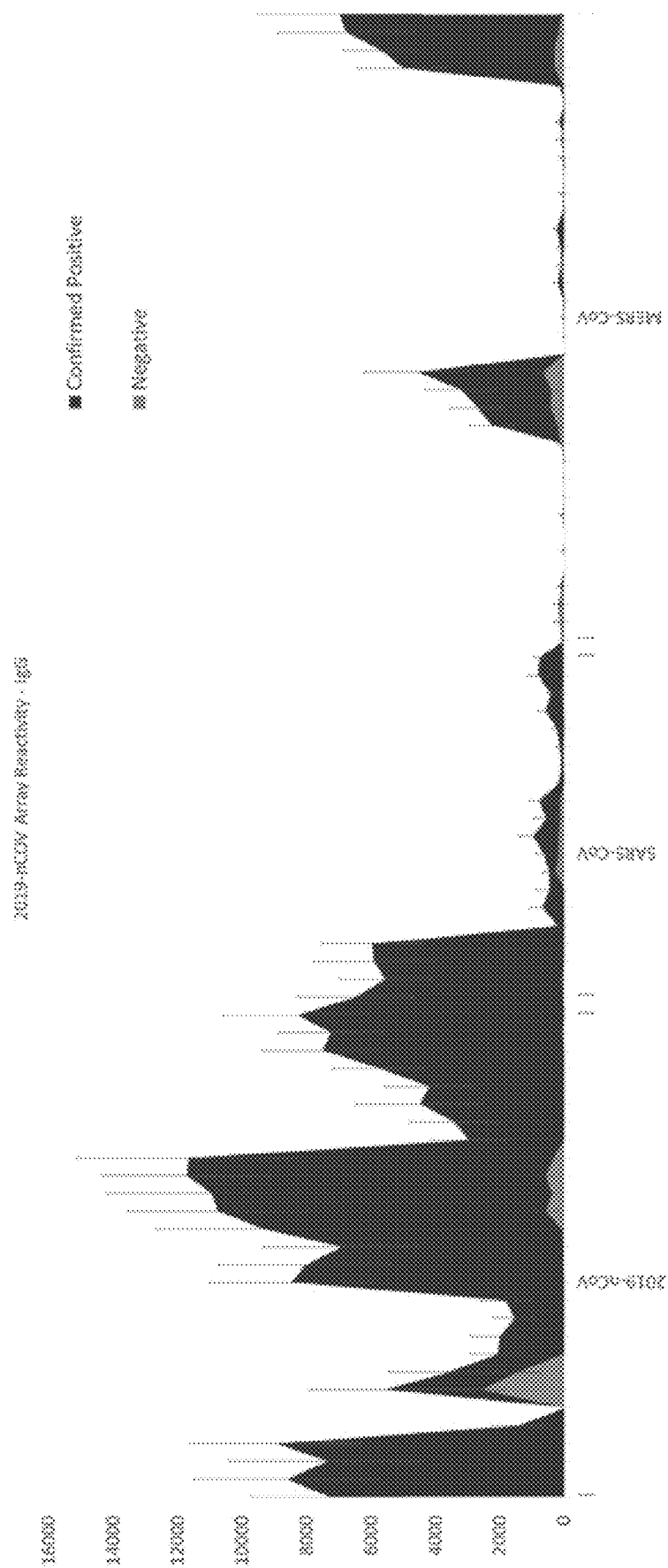

The "multiplexed antibody array" in disc 29 CD-1 provides an individual's virus "exposure fingerprint", the 'legacy antibody profile' reflecting past exposure and vaccination history. This array analysis approach is significantly more data rich (e.g. 67 antigens with 4 replicates per array) and is more quantitative than lateral flow assays in current use for measuring antibodies against the virus. To appreciate this point turn to FIG. 1 where we show both positive and negative 2019 nCOV Array Sensitivity IgG results obtained on blood samples from the COVID-19 Washington State 2020 outbreak Second, the sample collection device 100 described in connection with FIGS. 13a-13f is directly coupled into a disposable compact disc. The sample preparation steps are integrated on the fluidic disc and cloud-based data processing is implemented as described in connection with FIG. 15.

High throughput cloning and constructing microarrays 12 have previously been developed that contain human and animal antibodies with antigens from more than 35 medically important pathogens, including bacteria, parasites, fungi and viruses such as vaccinia, monkey pox, Herpes 1 & 2, Varicella zoster, HPV, HIV, Dengue, influenza, West Nile, Chikungunya, adenovirus, and coronaviruses. A DNA microarray 12 (also commonly known as DNA chip or biochip) is a collection of microscopic DNA spots attached to a solid surface. DNA microarrays 12 are used to measure the expression levels of large numbers of genes simultaneously or to genotype multiple regions of a genome. Each DNA spot contains picomoles ($10^{-12}$ moles) of a specific DNA sequence, known as probes (or reporters or oligos). These can be a short section of a gene or other DNA element that are used to hybridize a cDNA or cRNA, also called anti-sense RNA, sample, called target, under high-stringency conditions. Probe-target hybridization is usually detected and quantified by detection of fluorophore-, silver-, or chemiluminescence-labeled targets to determine relative abundance of nucleic acid sequences in the target. The original nucleic acid arrays were macro arrays approximately 9 cm×12 cm and the first computerized image based analysis was published in 1981. We have probed over 25000 samples from humans and animals infected with pathogens, and identified over 1000 immunodominant and candidate vaccine antigens against these pathogens. We have shown that the individual proteins/antibodies printed on these arrays 12 capture antibodies and/or antigens present in serum from infected individuals and the amount of captured antibody can be quantified using fluorescent secondary antibody.

In this way a comprehensive profile of antibodies that result after infection or exposure can be determined that is characteristic of the type of infection and the stage of diseases. Arrays 12 can be produced and probed in large numbers (>500 serum or plasma specimens per day) while consuming <2 µl of each sample. This microarray approach allows investigators to assess the antibody repertoire in large collections of samples not possible with other technologies.

Figure 3:
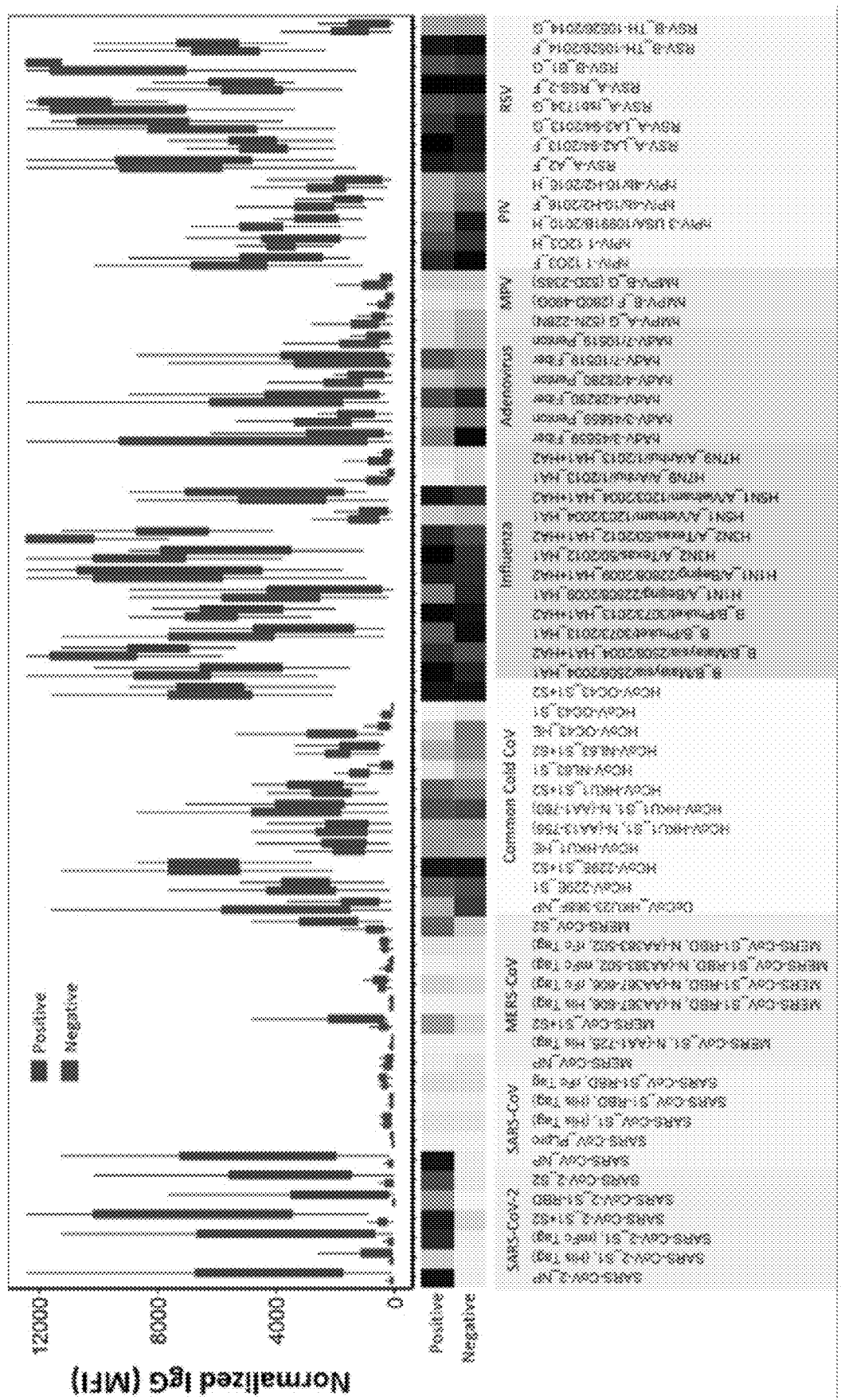
FIG. 3 is a graph of normalized IgG reactivity of positive and negative sera on coronavirus antigen microarray. The plot shows IgG reactivity against each antigen measured as mean fluorescence intensity (MFI) with full range (bars) and interquartile range (boxes) for convalescent sera from PCR-positive individuals (positive, red) and sera from naïve individuals prior to pandemic (negative, blue). Below the plot, the heatmap shows average reactivity for each group (white=low, black=mid, red=high). The antigen labels are color coded for respiratory virus group.

A coronavirus antigen microarray 12 (COVAM) was constructed containing 67 antigens that are causes of acute respiratory infections. The viral antigens printed on this array 12 are from epidemic coronaviruses including SARS-CoV-2, SARS-CoV, MERS-CoV, common cold coronaviruses (HKU1, OC43, NL63, 229E), and multiple subtypes of influenza, adenovirus, metapneumovirus, parainfluenza, and respiratory syncytial virus. The SARS-CoV-2 antigens on this array 12 include the spike protein (S), the receptor-binding (RBD), S1, and S2 domains, the whole protein (S1+S2), and the nucleocapsid protein (NP) as shown in the graph of FIG. 3. There is a similar set of antigens represented on the array from SARS-CoV, MERS-CoV, and the four common cold corona viruses.

Figure 2:
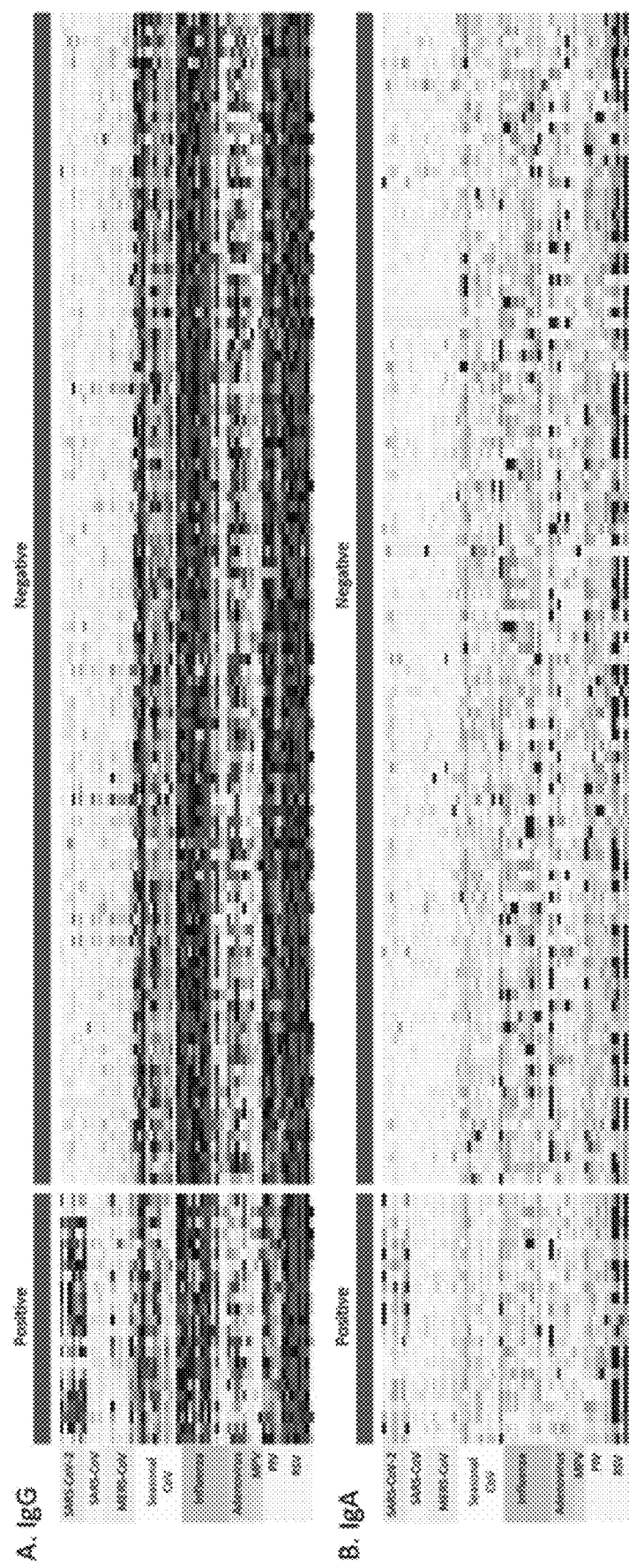
FIGS. 2a and 2b are heatmaps for coronavirus antigen microarray. The heatmaps show IgG of FIG. 2a and IgA of FIG. 2b reactivity measured as mean fluorescence intensity across four replicates, against each DNA dot in the microarray organized into rows color coded by virus, for sera organized into columns classified as positive or red (convalescent from PCR-positive individuals) or negative or blue (prior to pandemic from naïve individuals). Reactivity is represented below the heatmap by color (white=low, black=mid, red=high).

To determine the antibody profile of SARS-CoV-2 infection, the differential reactivity to these antigens was evaluated for SARS-CoV-2 convalescent blood specimens from PCR-positive individuals (positive group) and sera collected prior to the COVID-19 pandemic from naïve individuals (negative control group). As shown in the heatmaps of FIGS. 2a and 2b, the positive group is highly reactive against SARS-CoV-2 antigens. This is more evident for the IgG than for IgA. The negative controls do not react to SARS-CoV-2, SARS-CoV or MERS-CoV antigens despite showing high reactivity to the common cold coronavirus antigens. Positive group displays high IgG reactivity to SARS-CoV-2 NP, S2, and S1+S2 antigens and to a lesser degree SARS-CoV-2 S1 shown in FIGS. 2a and 2b. The positive group also demonstrates high IgG cross-reactivity against SARS-CoV NP, MERS-CoV S2 and S1+S2 antigens, while the negative group demonstrates low cross-reactivity with S1+S2 and S2 antigens from SARS-CoV-2 and MERS-CoV and no cross-reactivity against other SARS-CoV-2 antigens.

FIG. 26 contains the fluorescent intensity results for IgG shown in FIG. 18a, the Z-score statistics for the fluorescent results in FIG. 18c, the fluorescent intensity results for IgM shown in FIG. 18b, and the Z-score statistics for the fluorescent results of FIG. 1d. The Z-score shows how many standard deviations above or below the mean negative results a confirmed positive IgG or IgM sample is. Statistically significant z scores (5 or greater) have shaded numerals.

Antigens were then evaluated to discriminate the positive group from the negative group across a full range of assay cutoff values using receiver-operating-characteristic (ROC) curves for which an area-under curve (AUC) was measured. High-performing antigens for detection of IgG are defined by ROC AUC>0.85 as shown in FIG. 26. Four antigens are ranked as high-performing antigens: SARS-CoV-2 NP, SARS-CoV NP, SARS-CoV-2S1+S2, and SARS-CoV-2_S2. Additional high-performing antigens included SARS-CoV-2 S1 (with mouse Fc tag) and RBD, and MERS-CoV S2. The optimal sensitivity and specificity were also estimated for the seven high-performing antigens based on the Youden Index. Youden's J statistic (also called Youden's index) is a single statistic that captures the performance of a dichotomous diagnostic test. Informedness is its generalization to the multiclass case and estimates the probability of an informed decision. The lowest sensitivity was seen for SARS-CoV-2 S1, which correlates with the relatively lower reactivity to this antigen in the positive group. The lowest specificity was seen for SARS-CoV-2 S2, which correlates with the cross-reactivity for this antigen seen in a subset of the negative group. In order to estimate the gain in performance by combining antigens, all possible combinations of up to four of the seven high-performing antigens were tested in silica for performance in discriminating the positive and negative groups. The ROC curve with AUC, sensitivity, and specificity was calculated for each combination. There is a clear gain in performance by combining two or three antigens. For IgG, the best discrimination was achieved with the two-antigen combination of SARS-CoV-2S2 and SARS-CoV NP, with similar performance upon the addition of SARS-CoV-2S1 with mouse Fc tag (AUC=0.994, specificity=1, sensitivity=0.944). The addition of a fourth antigen decreased the performance.

FIG. 27 shows the performance data for combinations of high-performing antigens. ROC, AUC values and sensitivity and specificity based on Youden index for discrimination of positive and negative sera were derived for each individual antigen ranked, and high-performing antigens with ROC AUC>0.86 are indicated above the lines.

FIGS. 18a-d show an example of a single confirmed positive patient results. FIG. 18a shows the normalized fluorescent intensity for various IgG antibodies in a serum, with the two lines showing the average results for a confirmed positive (top) and confirmed negative (bottom). FIG. 18b shows the normalized fluorescent intensity for various IgM antibodies in a serum, with the two lines showing the average results for a confirmed positive (top) and confirmed negative (bottom). FIG. 18c shows the plotted Z-Scores for the IgG antibodies between a positive and negative result, with the three dotted lines representing the various Z-Score thresholds for mild, moderate and significant response. FIG. 18d shows the plotted Z-Scores for the IgM antibodies between a positive and negative result, with the three dotted lines representing the various Z-Score thresholds for mild, moderate and significant response.

We address some of the most urgent requirements to establish disease screening, interpretation and prevention goal by using the current COVID-19 pandemic as a most urgent target. The current POC COVID-19 detection platforms fall into three categories: 1) enzyme-linked immunosorbent assay (ELISA), Immunofluorescence Assays, 2) real time quantitative polymerase chain reaction (RT-qPCR), and 3) chest X-rays. Since a point of care method and device is the focus of this disclosure, chest X-rays are not addressed here.

The Optikus II

Figure 4:
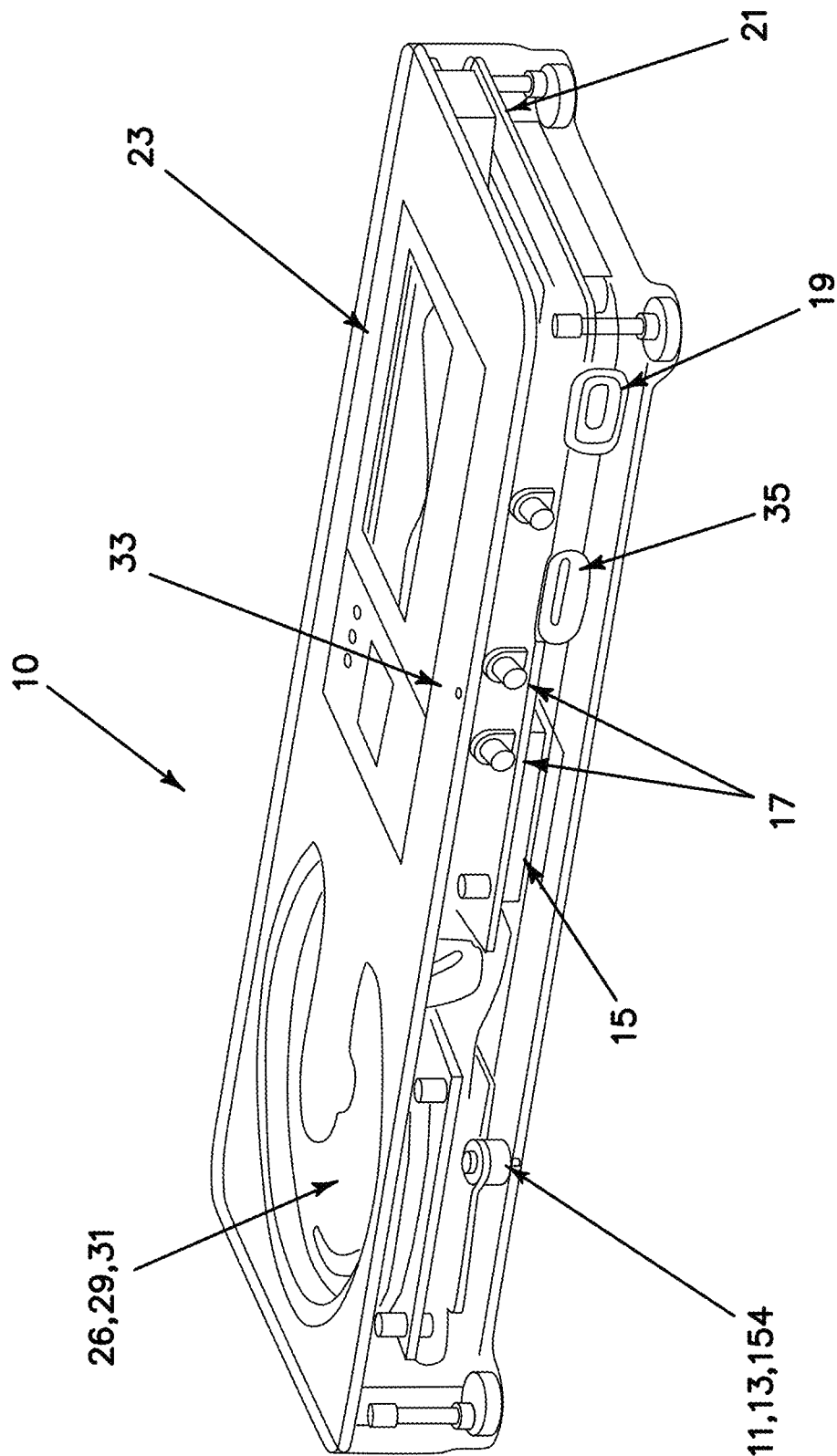
FIG. 4 is a perspective, partially transparent view of the Optikus II which processes a virus sample to quantify antigen specific antibody responses induced after infection. Sample preparation steps-depending on the assay—include: sample in, blood-plasma separation, plasma isolation, amplification or incubation washing, and measurement (SAW sensing for virus and fluorescence intensity detection for antibodies).

We have developed a rapid, portable diagnostic screening device, which uses compact disc (CD) microfluidics in a handheld instrument 10 to automate sample to cartridge introduction (blood capillary or swab), sample preparation (e.g. metering, dilution, blood plasma separation and cell lysis), reagent storage and quantitative measurements using a SAW sensor 90 (for direct virus measurements) and a fluorescence camera 89 (for protein array measurements for a large number of different assay targets as represented by the instrument 10 shown in the perspective view of FIG. 4. Shown in FIG. 4 is also a microfluidic disc interface 11 including a Z-stage motion platform 13 and disc spindle motor 154, SAW RF shields 15, multifunction buttons 17, a SD card 35, a USB port 19, speaker and microphone 21, touch display 23 and status LEDs 33 better described in the incorporated specification.

The Optikus instrument 10 also contains thermoelectric heating and cooling or Peltier elements 142 in disc CD-1 shown in FIG. 19, and a temperature control mechanism in disc CD-1 (not shown) for performing RNA and DNA amplification using either therrnocycling or isothermal amplification directly on the microfluidic disc 26 (CD-3). The Optikus platform is unique in its ability to rapidly accommodate new tests by changing the microfluidic disc design and assay components. For example, Optikus II performs two COVID-19 test sets with disc 29, CD-1 as described in the incorporated specification (for Elisa detection with a SAW), and disc 31, CD-2 (for immunofluorescence detection). The development of the third cartridge (CD-3 for RT-qPCR) is also within the intended scope of the invention as described in the incorporated specification. The present specification is primarily directed to the disclosure of instrument 10 configured to perform immunofluorescence detection using microarrays 12 in disc 31, CD-2. Instrument 10 in FIG. 19 has the necessary circuitry and detectors to accommodate or operate all three types of discs 26, 29, and 31 for Elisa detection with a SAW, immunofluorescence detection and RT-qPGR.

The Optikus II reader 10 contains various additional components for making measurements with various types of biosensors and microfluidic CD's. FIG. 19 shows a top transparent perspective view of the Optikus 11 reader 10 with the microfluidic assembly bay 136 opened, which includes the laser 138 for ablating various microvalves in the microfluidic CD 26, 29, 31, a SAW RF interposer 140 for making RF measurements using SAW detector 90, various Peltier elements 142 for regulating temperature on the disk, and a CMOS camera 89 for making various fluorescent imaging measurements.

FIG. 23 is a high level block diagram of instrument 10 in which SAW reader 135 is coupled to a sensor interface 137 and provided an RE excitation signal to SAW 90. Reader 135 includes USB interfacing, power, serial data interfacing, display control and wireless communication. Control of the microfluidics on disc CD-2 is controlled by reader 135 through a microfluidic controller 133 which include processor control of a laser and disc motor. The detail operation of instrument 10 of FIG. 23 is set out in the incorporated specification.

FIG. 24 is a high level block diagram of instrument 10 in which serology-PCR reader 129 is coupled to camera 131. This high level block diagram illustrates how the reader 129 with camera 131 acts as both the camera for the serology solution, and also acts as the reader for a chemilumunescent PCR solution. Reader 129 can do both PCR and serology. Reader 129 in the illustrated embodiment is based on a Raspberry PI single board computer and includes USB interfacing, power, serial data interfacing, display control and wireless communication. Control of the microfluidics on disc 26, CD-3, is controlled by reader 129 through a serology microfluidic controller 127 which includes processor control of a laser, disc motor and thermoelectric (TEC) heating and cooling control of Peltier element 142. The detail operation of instrument 10 of FIG. 23 is set out in the incorporated specification.

FIG. 25 is an illustration of disc 26, CD-3, and the immunoPCR steps which are automatically carried out on it. Similar steps are described in detail in the incorporated specification. A blood sample taken from a finger prick at step 65 is disposed into sample chamber 67. The blood and serum are automatically separated in blood-serum separation chamber 63 at blood serum separation step 61. The serum is transferred to mixing chamber 59 and mixed with and conjugated to the target 53 an antibody DNA complex at step 57. The conjugated target 53 is transferred to mixing and replication chamber 55 where it is mixed and conjugated with an antibody-magnetic nanoparticle (MNP) complex with a DNA tag as more fully described in the incorporated specification. The plasma is removed at step 47 by transfer to plasma waste chamber 49. A buffer from wash reservoir 45 delivered to chamber 55 through chamber 59 removes the unconjugated DNA at step 46. The conjugated antibody-target complex is resuspended at step 77 in an amplification buffer supplied to chamber 55 from amplification buffer chamber 79. Isothermal amplification is then performed in chamber 55 during replication or PCR step 81. The replicated DNA tags are then transferred to and bound in imaging chamber 87 at step 103. Optional washing and spin drying steps 105 removing unbound DNA tags to waste chamber 107 may be performed if necessary to improve imaging results. Additional supporting detail concerning the method illustrated in FIG. 25 is provided in the incorporated specification.

FIG. 21 is a block diagram of the circuitry used in microarray reader 134 of the Optikus instrument 10 for reading a disc 29, CD-1. The analogous block diagram of the circuitry used for a reader employing a SAW 90 as the detector is discussed in detail in the incorporated specification. Disc 29 is shown to diagrammatically include a loading chamber 70 from which the sample is transferred to a blood-plasma separation chamber 72. Magnetically tagged elements are acted upon by magnet/cavity 153 and sensed by light and a magnetic field controlled through magnetic and optical index driver 157 coupled to microprocessor 148. The magnet 153 acts as an indexer, whereby every time the magnet 153 in the disk 29 passes over a magnetic sensor (not shown), the position of the disc 29 can be checked by the reader 134. The disc position is then compared against the index on the motor 154 and a correction is applied if needed. The off-motor indexer can thus be realized with an optical sensor and a reflective sticker or a magnet on the disc 29 and a magnetic field sensor.

As the separated plasma is transfer from chamber 72, the plasma is measured by photodetection circuit 71 coupled to LED driver 73 and the returned signal amplified by opamp 75, both of which circuits 73 and 75 are coupled to and controlled by microprocessor 148. Laser 138 used to selectively open valves in disc 29 is controlled through laser driver 139 and opamp 141, both controlled by microprocessor 148. The processed sample is transferred to reaction-detection chamber 76 in disc 29, where it is reacted with the DNA dots on microarray 12. Camera 164 takes a color photo of microarray 12 and the image is communicated via image signal processor 166 to microprocessor 146. Clocked processor 146 under program control stored in RAM memory 147 and flash memory 149 format the microarray data and communicate it through wireless module 168 to cloud service 106 as further described in connection with FIG. 22.

Reader 134 is controlled by two microprocessors 146, 148, one processor 146 located on the main off-the-shelf (OTS) board 150 and one processor 148 on the microfluidic board 152. Microprocessor 148 on microfluidic board 152 controls the spindle motor 154 with encoder through motor driver 155, geared motor 156 with encoder driven by motor driver 159 and limit switches 158 coupled through low pass filter 161, which motor 156 spins the disk 29 and allows it to be placed in a selected or controlled angular position for measurement. The microfluidic board 152 controls the IR LED 160 through LED driver 162 for excitation of the fluorophores. The CMOS camera 89 is controlled by the main board OTS 150 through an image signal processor 166. The main board OTS 150 controls the Wi-Fi module 168, Bluetooth module (not shown), digital display 170, and power interface 172. Microprocessor 148 running under program control stored in memory 151 adjusts environmentally dependent operations within disc 29 using temperature and humidity sensor 145.

Similar circuit diagrams for use with disc 26, CD-3, and disc 31, CD-2 are included in the appendix and will not be further discussed here.

The Assay—Protein Arrays

The protein microarray 12 utilizes the probes of the Optikus II instrument 10 and analyzes the target to quantify antigen specific antibody responses induced after infection from any microorganism. In the array 12 about 70,000 proteins from 35 infectious agents have been probed and analyzed using DNA spots printed on the protein microarray 12. The array 12 has been probed with thousands of serum specimens from infectious disease cases and controls to identify the specific antigens that induce antibodies after infection. This array 12 is particularly relevant today with the coronavirus outbreak because of the urgent need to understand who in our environment has been exposed to the virus, to predict who are susceptible to severe, mild and asymptomatic infection, identify who has been exposed and has protective Abs, and who are unknowingly spreading the infection to close contacts. Serosurveillance data of this kind can locate 'hot spots' where the infectious agent is present in the local population and public health mitigation and containment Measures should be concentrated.

Figure 5:
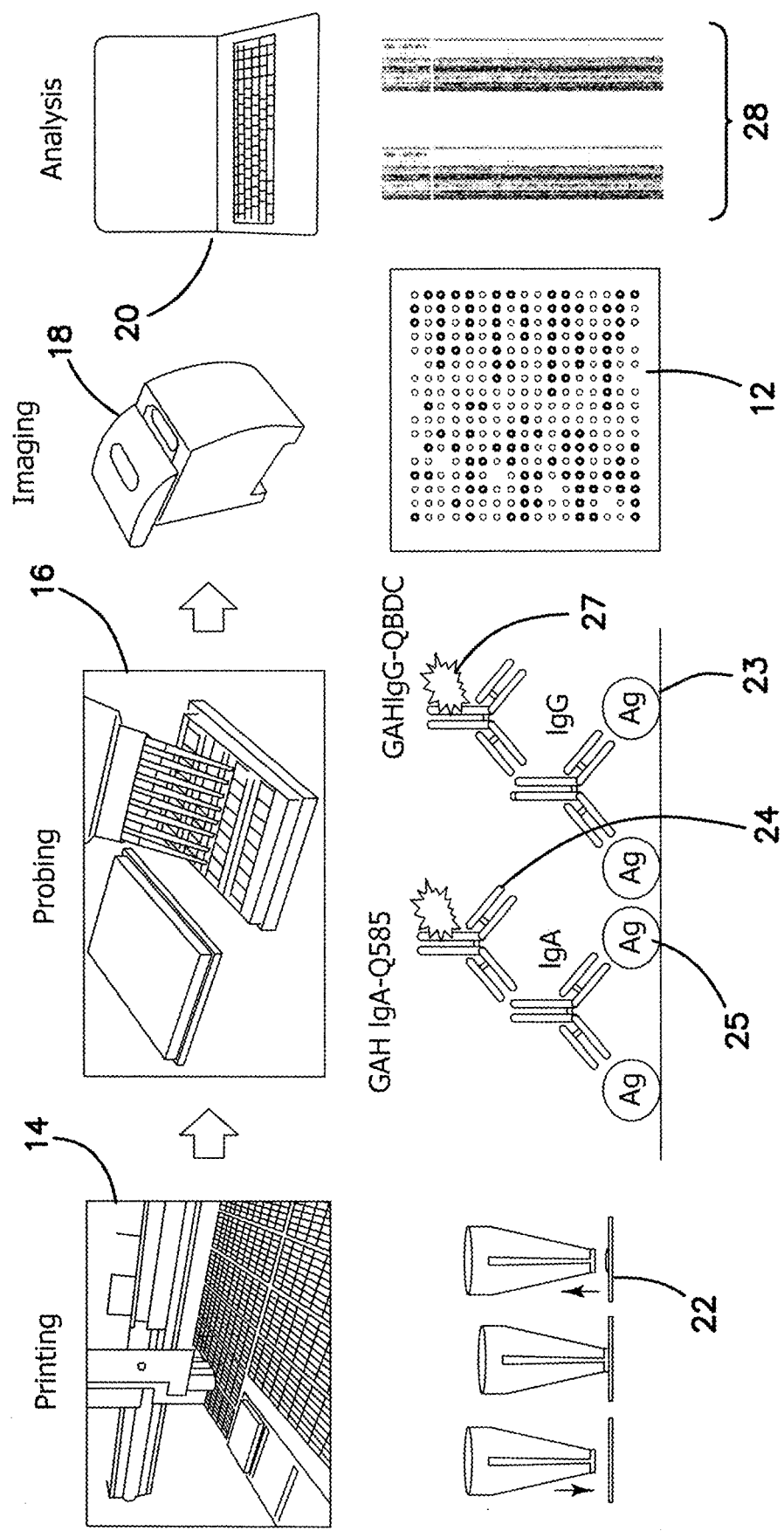
FIG. 5 is a diagram illustrating the assay procedure in the microarray as carried out on a laboratory benchtop.

The current open benchtop workflow is illustrated in FIG. 5 with four steps: 1) microarray printing step 14, 2) probing step 16, 3) imaging step 18, and 4) analysis step 20. The microarrays 12 are used to quantify and identify the Ab responses induced after an infection. Currently the capacity for each of the steps identified in FIG. 5 is as follows. Printing step 14 uses a conventional protein microarray printing facility that can print 1.4 million protein antigen spots 22 per day onto 4,800 microarrays. Probing step 16 is a benchtop probing method that allows 500 hundred serum specimens to be probed on the microarrays 12 per day by conjugating a specific fluorescent tag 24, 27 to a corresponding antibody 23, 25. Quantification or imaging step 18 uses a robotic laser scanner to quantify the level of Abs that bind to the antigens printed on the array 12. Analysis step 20 uses software to organize and help interpret the results 28 of the tests of array 12 (see examples in FIGS. 1a and 1b).

Assay Modification Steps for Use on CD

In order to adapt the microarray assays described in relation to FIG. 5 to the CD based fluidics platform of instrument 10, a mini-antigen and antibody array 12 is prepared containing antigens or antibodies from or against the following viruses: SARS-CoV-2, SARS-CoV-1, MERS, influenza, adenovirus, parainfluenza, metapneumovirus, and respiratory syncytial virus. The whole probing process takes about 15 minutes. Briefly, 10 μl of plasma for detection of antibodies on antigen array 12 or nasal swab samples for detection of viral antigens on antibody array 12 are disposed at step 32 in FIG. 6 directly onto the dry preblocked array 12. After incubation for 5 minutes, 10 μl of fluorescence labelled secondary Ab at step 34 is added while pushing samples out of the array chamber. Arrays 12 are washed at step 36, centrifuged to dry at step 38, and then are ready for image capture at step 40 on up to three colors using a fluorescent camera for different Ig isotypes from plasma samples. Images are then sent to cloud for analysis.

FIG. 20a is a diagram illustrating a fluorescence measurement of a microarray 12 being made in disc 29 with a CMOS fluorescence camera 89. An LED 91 emit fluorescence excitation photons, which pass through a preliminary emission light filter 84 which has a bandpass peak of 750 nm. The filtered excitation photons interact with the microarray 12 mounted on a nitrocellulose membrane 85 carrying the fluorophore microassay 12. The sample interacts with microarray 12 within reaction chamber 56. The excited or induced emitted fluorescent photons then travel through the camera notch filter 83 centered at 790 nm, which then is collected by the CMOS color camera 89 and sent to the microarray reader 134 for processing and communication to the cloud service 106.

FIG. 20b shows the spectral graph of the absorption of the fluorophore or excitation spectra 41 and emission of the fluorophore or emission spectra 43. Superimposed on the excitation spectra 41 and emission spectra 43 is the bandpass of the LED emission filter 84 and notch filter 83. Filter 84 confines the excitation light from LED 91 to a wavelength range overlapping with the lower half of the fluorophore excitation spectra of the DNA spots 22 on microarray 12. Notch filter 83 limits the wavelengths received by camera 89 to the greater domain of the emission spectra 43, while completely nonoverlapping with the bandpass of filter 84. Thus, the color image produced by camera 89 is only that of the excited fluorophores in the DNA spots 22 of microarray 12 and not of any of the excitation light from laser 91.

Additionally, the figure indicates the presence of two cutoff filters defining the boundary of LED excitation vs the CMOS camera detection.

Alternatively, the array 12 can also be adapted for developing a neutralizing antibody assay as diagrammatically depicted in FIG. 7. Arrays 12 spotted with receptor binding domain (RBD) of spike protein are probed with plasma samples from patients and fluorophore labelled ACE2 (e.g. Alexa Fluor 488) at step 42, another fluorophore (e.g. Alexa Fluor 647) labelled secondary antibody against human IgG (for detection of RBD antibody in the sample) at step 44 is added while pushing samples out of the array chamber. Arrays 12 are then washed at step 6, centrifuged to dry at step 48, and are ready for image capture at step 50 on two colors for RBD antibody present in patient samples and ACE2 respectively. Samples without neutralizing antibodies or RBD antibodies are detected with ACE2 fluorescence, while samples with RBD antibodies or increasing amount of neutralizing antibodies that interfere with ACE2-RBD binding are detected with a decreasing amount of ACE2 fluorescence. In the absence of RBD antibodies from plasma samples, the amount of ACE2 fluorescence can be quantified for relative neutralizing activity. Serum samples can be directly applied onto the CD platform and processed for image acquisition. This simplifies the design of fluidics system.

Protein Array Assay Adaptation to Deployment in CD-1

Although the approach illustrated in FIGS. 5-7 works well in a lab setting, it has several limitations that prevent its more widespread field deployment. For example, using open wells is obviously impossible in a POC setting and the cost of a laser scanner also is prohibitive in such a setting. Instead we have developed a 10-minute automated POC coronavirus antigen microarray with one array enclosed per disposable fluidic disc CD-1 cartridge. For quantification, digital fluorescent microscopes are used. To implement this scenario the protein array printing remains the same as disclosed above, except that we now must put methodology in place for large commercial scale-up production.

Array Cutting

Although multiple arrays 12 are normally manufactured in a batch process on a substrate, a single array 12 is used per cartridge (disc CD-1) attached to a corresponding nitrocellulose film slide. The arrays 12 for incorporation in disc CD-1 simultaneously probes 60 antigens from 12 known coronaviruses, along with several types of adenovirus, RSV, metapneumovirus, parainfluenza and influenza viruses. This test can reveal IgG, IgA and IgM seroreactivites to different viruses and is useful to determine the seroprevalence of the SARS-CoV-2.

CD Fluidics

Figure 8A:
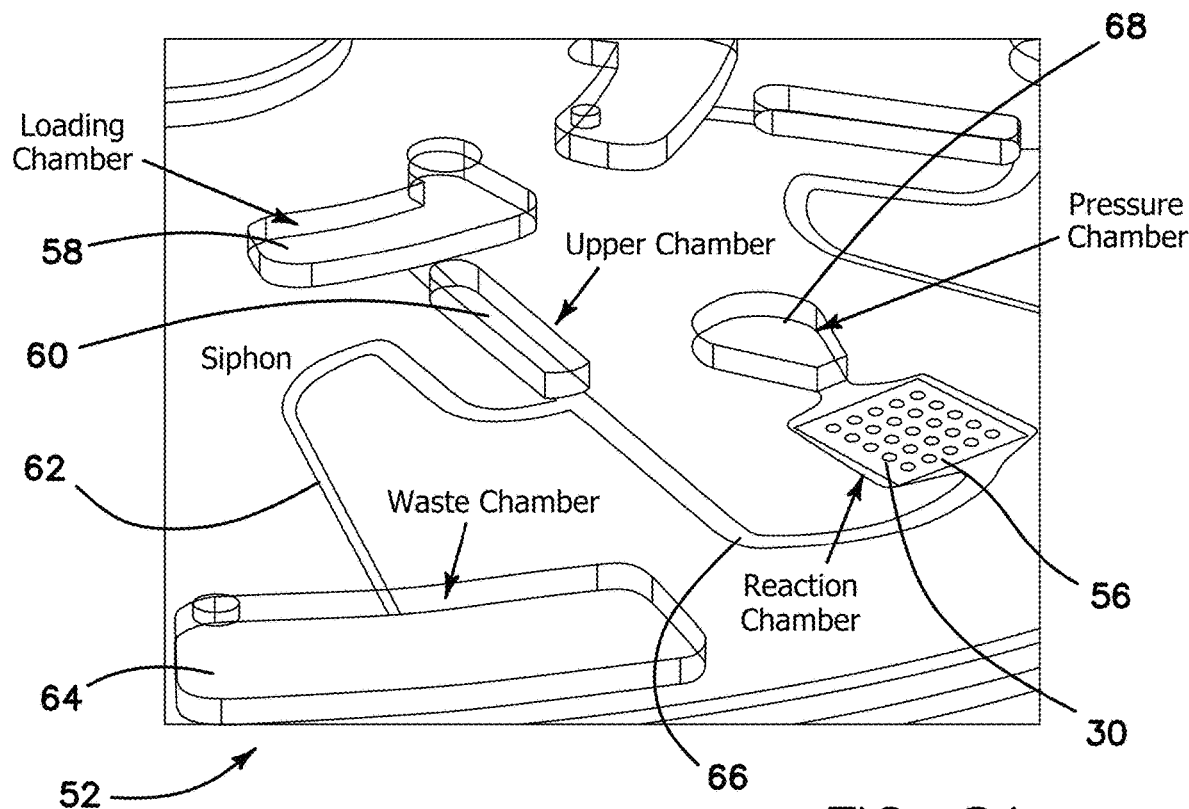
FIG. 8a is a schematic illustration of the fluidic system in disc CD-1.
Figure 8B:
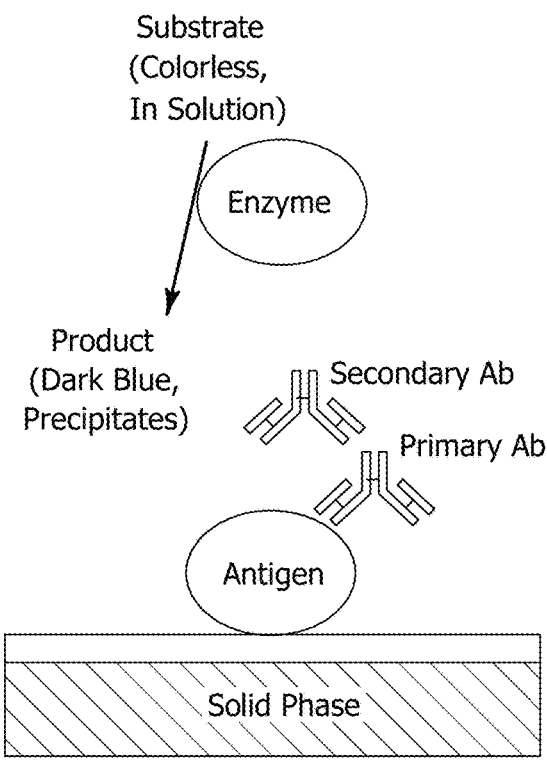
FIG. 8b is a schematic illustration of antibody capture at each array element. The reaction chamber holds the spotted protein array.
Figure 9:
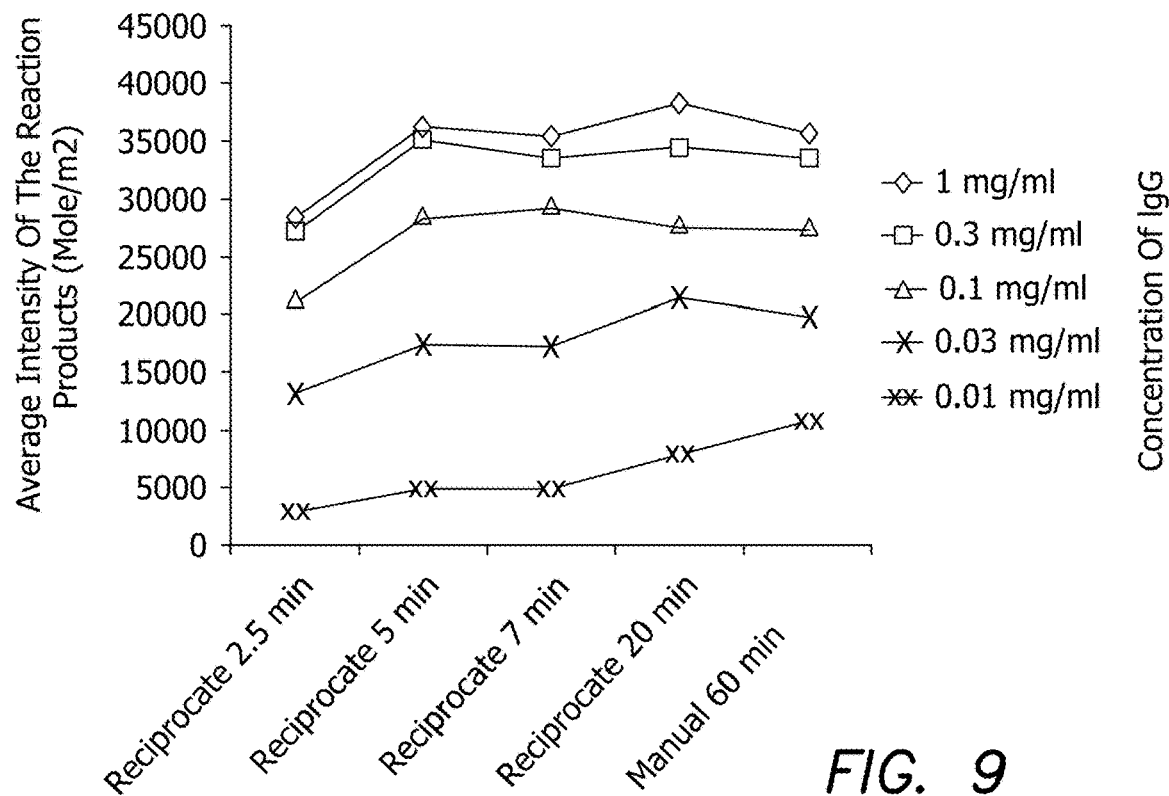
FIG. 9 is a graph of experimental results comparing the intensities of IgG microarrays developed using the reciprocating flow system with different incubation times and intensities of IgG microarrays developed using the manual method with incubation time of 1 hr.

FIGS. 8a and 8b show a CD system for low cost and high throughput automated immunoassay processing. The disposable immunoassay disk design includes a fluidic structure that enables very efficient micro-mixing based on a reciprocating mechanism in which centrifugal acceleration acting upon a liquid element first generates and stores pneumatic energy that is then released by a reduction of the centrifugal acceleration, resulting in a reversal of direction of flow of the liquid. Through an alternating sequence of high and low centrifugal acceleration, the system reciprocates the flow of liquid within the disk to maximize incubation/hybridization efficiency between antibodies and antigen macromolecules during the incubation/hybridization stage of the assay. A schematic illustration of the fluidic system 52 and of antibody the capture 54 at each array element is shown in FIG. 8a. The reaction chamber 56 in FIG. 8a holds the spotted protein array 12. The sample is loaded into loading chamber 58 of the CD and through centrifugal force transferred to upper chamber 60. It is also transferred via duct 66 to reaction chamber 56, where it is probed by array 12. Excess sample is transferred to siphon 62 and disposed of in waste chamber 64.

For proof of concept, we set up an immune-screening experiment by making arrays of *Burkholderia* antigens and probing them with infected and naive sera. The characteristic enzyme of the sample, which is colorless in solution, is conjugated via the secondary and primary Ab to the antigen captured on array 12. The product fluoresces as a dark blue precipitate. *Burkholderia* is a bacterial pathogen that attacks the human respiratory system and causes melioidosis. Symptoms may include pain in the chest, bones, or joints, cough, skin infections, lung nodules.

The main considerations driving the miniaturization and automation of immunoassays are the high cost of reagents such as antibodies and antigens, the high cost of qualified labor, and the long assay times involved. We have demonstrated, based on proof-of-concept results, that by using the described reciprocating fluidic system we were able to perform an immunoassay with a ~75% reduction in reagent consumption and a ~85% reduction in assay time. See FIG. 9.

The system implemented in disc CD-1 is simplified because: (1) blood samples can be used, (2) fluorescence instead of absorption measurements are used so that no timing needed, and (3) the quantification is carried out using inexpensive digital fluorescent microscopes.

FIGS. 10*a*-10*c* are graphs that show simulation results. FIG. 10*a* compares three modes of incubation: Single flow through, reciprocating flow, and passive diffusion between human IgG antigens and a goat anti-human IgG antibodies. FIG. 10*b* shows the effect of the antibody concentration on the rate of complex formation. Antigen-antibody complex formation decreases and reaches an equilibrium state in a longer time as the initial concentration of the analyte decreases. FIG. 10*c* shows the Influence of the flow Reynolds number on the rate of complex formation. Antigen-antibody complex formation increases and reaches an equilibrium state earlier as the flow velocity increases. This difference is more visible for antibodies with smaller initial concentration.

Besides reciprocation, other fluidic functions that we are implementing on disc CD-1 are: 1) sample metering, 2) blood plasma separation and 3) fluorescence detection. In FIG. 11*a* these functions are illustrated with a protein array 12 and a CMOS chip including a laser diode and CCD detector below the CD for signal readout. The sample is loaded into sample loading chamber 70 of the CD and transferred by centrifugal force to the blood-plasma separation chamber 72. The target bearing plasma is transferred via siphon 74 into reaction-detection chamber 76, which may selectively be optionally communicated with valved washing buffer from chamber 78, and optionally conjugated with gold nanoparticle for mass enhancement from chamber 80 and with an air pocket of chamber 82 for reciprocation. Detection is realized by use of a 650 nm diode laser directed onto the array 12 in chamber 76, which is read by a Si-CCD array positioned below the CD.

In FIG. 12 we show how a blood sample is acquired from a finger prick and collected in a 300 μL microvette 88 (CB 300). A blood droplet 39 is drawn by a finger prick by a telescopic microcapillary 37 and drawn into cavity 71. Microcapillary 37 is telescopically drawn into cavity 71 and microcuvette 88 sealed with cap 68. When the sample is to be delivered to disc 26, 29 or 31, microcapillary 37 is telescopically extended and the blood from cavity 71 is transferred via the microcapillary 37 by capillary action into the sample loading chamber 70 of the CD rotor 86, where the first steps involve sample volume metering and blood plasma separation as described above.

Direct COVID-19 Assay Adaptation to Deployment in CD-2

If results on the disc 29 CD-1 are positive for the presence of the virus antibodies, CD-2 disc 31 is used for a rapid (<12 minutes), point-of-care diagnostic test for direct detection of COVID-19 from nasal swab samples. The CD-2 utilizes a surface acoustic wave biosensor 90 (SAW) for direct COVID-19 detection. In the past, the SKC SAW sensor 90 has successfully detected multiple high-profile bacteria and viruses, including Ebola, and anthrax. Over the last two years, we have significantly improved the sensitivity and detection capability of the SAW biosensor 90. The sample introduction from a swab tip 95 into CD 31 is shown in FIG. 13a-13f and the SAW sensor 90 mounted in an SKC disc 31 is shown in FIG. 14. In the embodiment of FIG. 14 disc 31 includes two SAW sensors 90 with a fuzz button connector 101.

Figure 13F:
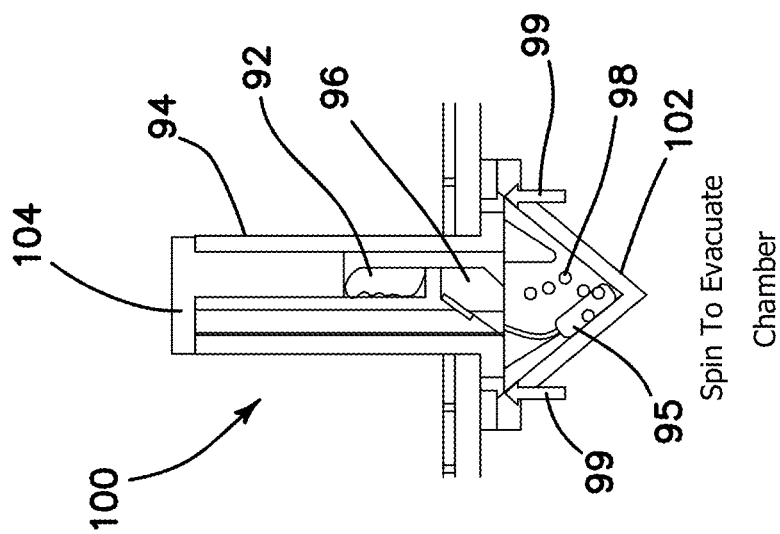
Figure 13E:
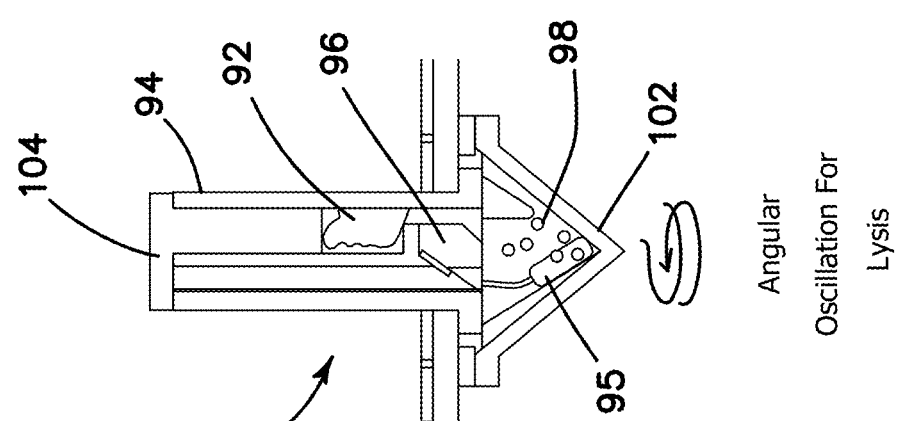
Figure 13D:
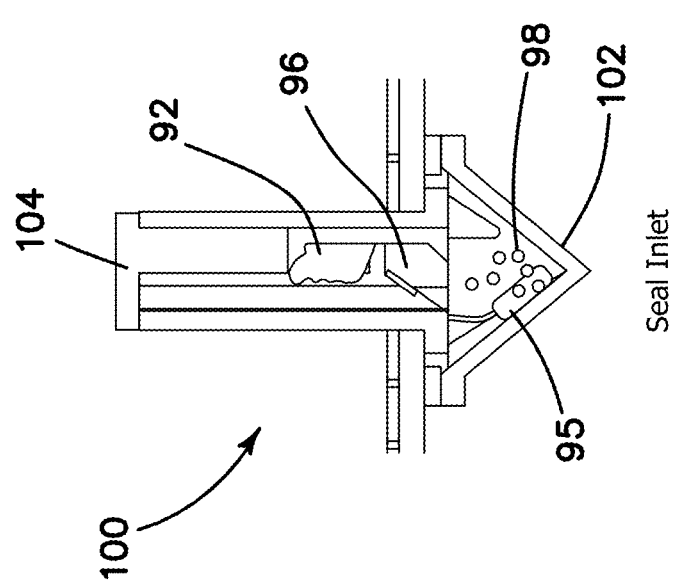

FIGS. 13a-13b are cross sectional views of a cone device 100, which is inserted into disc 31 prior to loading disc 31 into instrument 10. Cone device accepts a nasal swab 94, cut it, resuspend with buffer and lysis beads 98, release reagents 93, perform cell lysis, and evacuate sample onto the disc 31. Reagent pouch 92 is a chamber for containing a selected reagent to treat the sample from swab 94. Swab tip 95, bearing the target sample, is fully inserted into swab chamber 102 as shown in FIG. 13a, sliding past downwardly inclined blade 96 without being cut. Pulling swab shaft 94 upward forces shaft 94 into downwardly inclined blade 96 against the swab shaft 94 cutting it and allowing the distal end of swab 94 to remain in the bottom of the device 100 as shown in FIG. 13b as swab shaft 94 is removed from device 100. The sealing cap 104 is pushed down as shown in FIG. 13c bursting open the buffer pouch 92 and allowing the reagent or buffer 93 to flow through duct 97 to the swab chamber 102 and contact the severed swab tip 95. The sealing cap 104 is fully pushed down to seal the inlet to device 102 as shown in FIG. 13d. Device 100 is manually angularly oscillated as shown in FIG. 13e to cause lysis of the sample target. Free metal beads 98 in the swab chamber 102 are present and assist in lysis during agitation. Device 100 is then manually spun to evacuate the swab chamber 102 through peripheral openings as indicated by arrows 99 and to transfer out the lysed target sample as shown in FIG. 13f.

The SKC Optikus Cloud infrastructure

As an Internet-of-Things (IoT) device, the Optikus II instrument 10 provides data critical to the diagnosis of illnesses and diseases. The Optikus II measurements are transmitted to a cloud service 106 over an encrypted, secure HTTPS link using a device API 108 as shown in FIG. 15, which is a local Optikus cloud. The cloud service 106 is a micro-services API platform using current best practices for security, resiliency, and reliability. This allows permissioned access to test results from hospitals 112, doctors 114, and the patients 110 themselves. Test results are stored in an Oracle database 116 for Deep Learning analysis and stored in a distributed ledger technology 118 (DLT) or blockchain database, assures transparency, high availability, and immutability of the data.

FIG. 16 illustrates the steps of processing image data output from a digital, fluorescent imaging-enabled Optikus II instrument 10 used in combination with Cloud-based data processing. In step 120 a sample is obtained from the patient in the field and probed on instrument 10 as described above. An image of microarray 12 is obtained by instrument 10 in step 122 and uploaded into the cloud in step 124 to cloud server 106. The detected antigens or antibodies are quantified from the uploaded data at step 126 and subject to further data processing at step 128. The resultant data is then made available to individual patient and public health data analysis at step of 130. The data and its analysis is then made available to clinical testing at step 132, namely integrating with the Oracle cloud network 106 to compile all clinical test data, so that the analyzed data is made available immediately to the point-of-care site.

FIG. 22 a more detailed illustration of cloud ecosystem 176, 178, 180 to interface instrument 10 with a user cellphone 174, receive microarray data, compute the diagnostic results, and return the diagnostic analysis to the cellphone 174. In the illustrated embodiment a user or patient seeking to be tested for Covid-19 using his phone 174 registers online with an Oracle data management system (DMS) 176 through a registration module 182. The user identifies him or herself and is scheduled by module 184 for one or more specified tests at a specified date, time and place near the user and all relevant data is accumulated for the user in database 186. The patient-test event is assigned a unique quick response (OR) code and is sent to the user's phone 174 as a short message service (SMS) text through module 188.

The user arrives at the testing site 180 at the scheduled appointment and uses his or her assigned QR code to identify him or herself and the check in event is processed by module 190 and accumulated in the user's data record in database 186. The data associated with the QR code is read or scanned by instrument 10 at the testing site 180 identifying the patient and the test or tests to be undertaken. The test(s) is or are performed at step 194 with instrument 10 as described above. After the sample is taken, all steps in the ecosystem 176, 178, 180 are automatic and occur in sequence under software control without the need for further human intervention. The assay performed, assay data uploaded, analyzed, stored, diagnosis is made, and results reported out to the patient in an hour or less, and usually within tens of minutes. A color photographic microassay record is created as a tagged image file formatted (TIFF) or other graphically formatted file at step 196. The color photographic microassay record is packaged with the QR scan code at step 198 by instrument 10 and sent to the testing service cloud site 178, where it is wirelessly received at step 200 and uploaded into the database 202 of testing service cloud site 178. The assay results are processed and a diagnosis based on the testing generated at step 204 and converted to JavaScript object notation (JSON). JSON is an open standard file format, and data interchange format, that uses human-readable text to store and transmit data objects consisting of attribute-value pairs and array data types (or any other serializable value). It is a very common data format, with a diverse range of applications, such as serving as a replacement for XML in AJAX systems. The resulting JSON and TIFF files are communicated via the internet at step 206 for storage in object storage 208 in Oracle DMS 176 and thence to database 186 for insertion into the patient's record. The completed results are then communicated from a results portal 210 to the user's phone 174. The entire process is automatically performed in 30-60 minutes or less. The benchmark events are automatically shared between the user's phone 174 and Oracle DMS 176 with a health care partner's (HCP) phone 212, who may then implement or initiate medical intervention as necessary. In the event that further diagnostic steps are desired or public heath reporting and responses are needed, future processing is performed relative to the testing cloud service 178 through module 214 and independently by Oracle cloud DMS 176 through module 216.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings.

Thus, if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

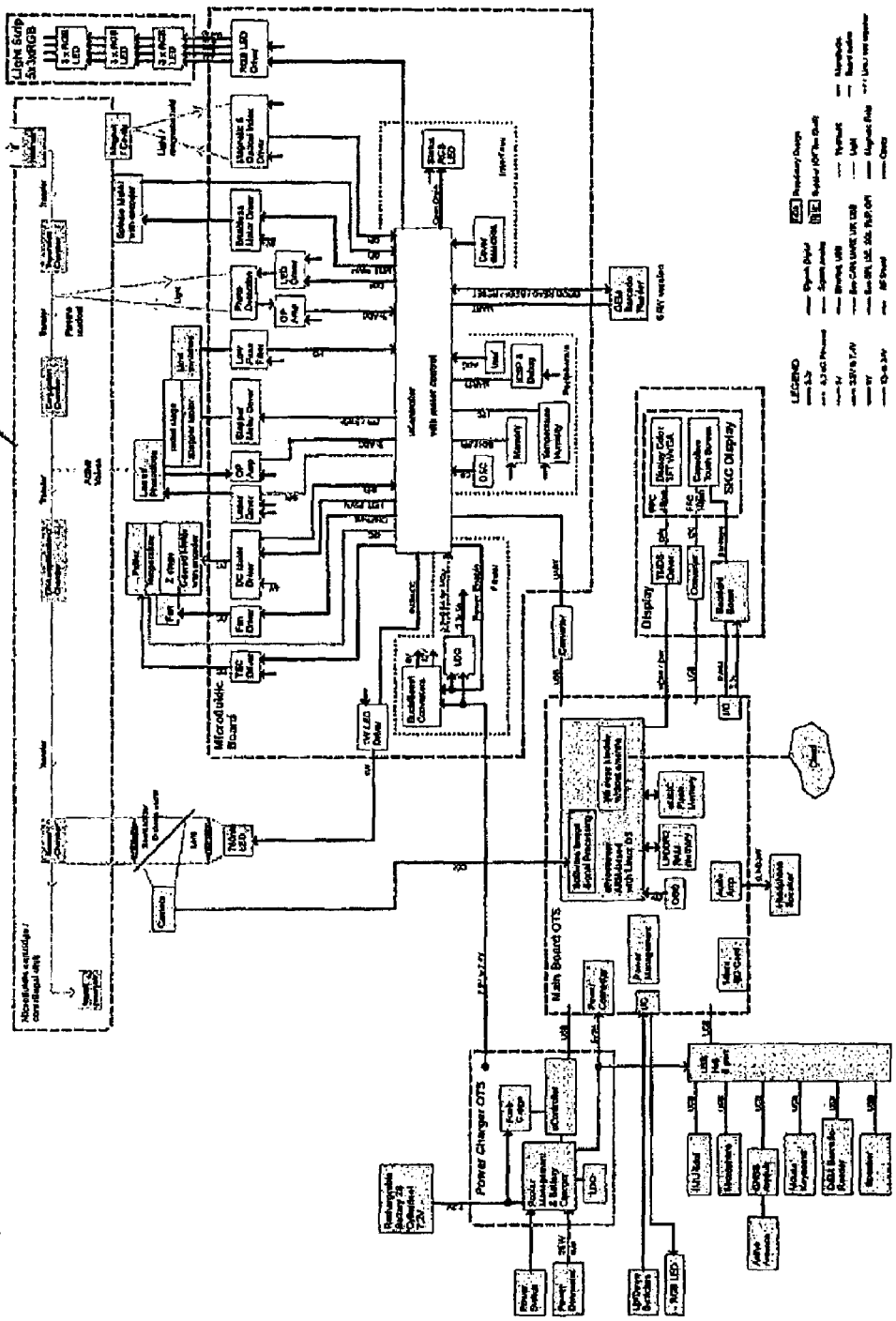

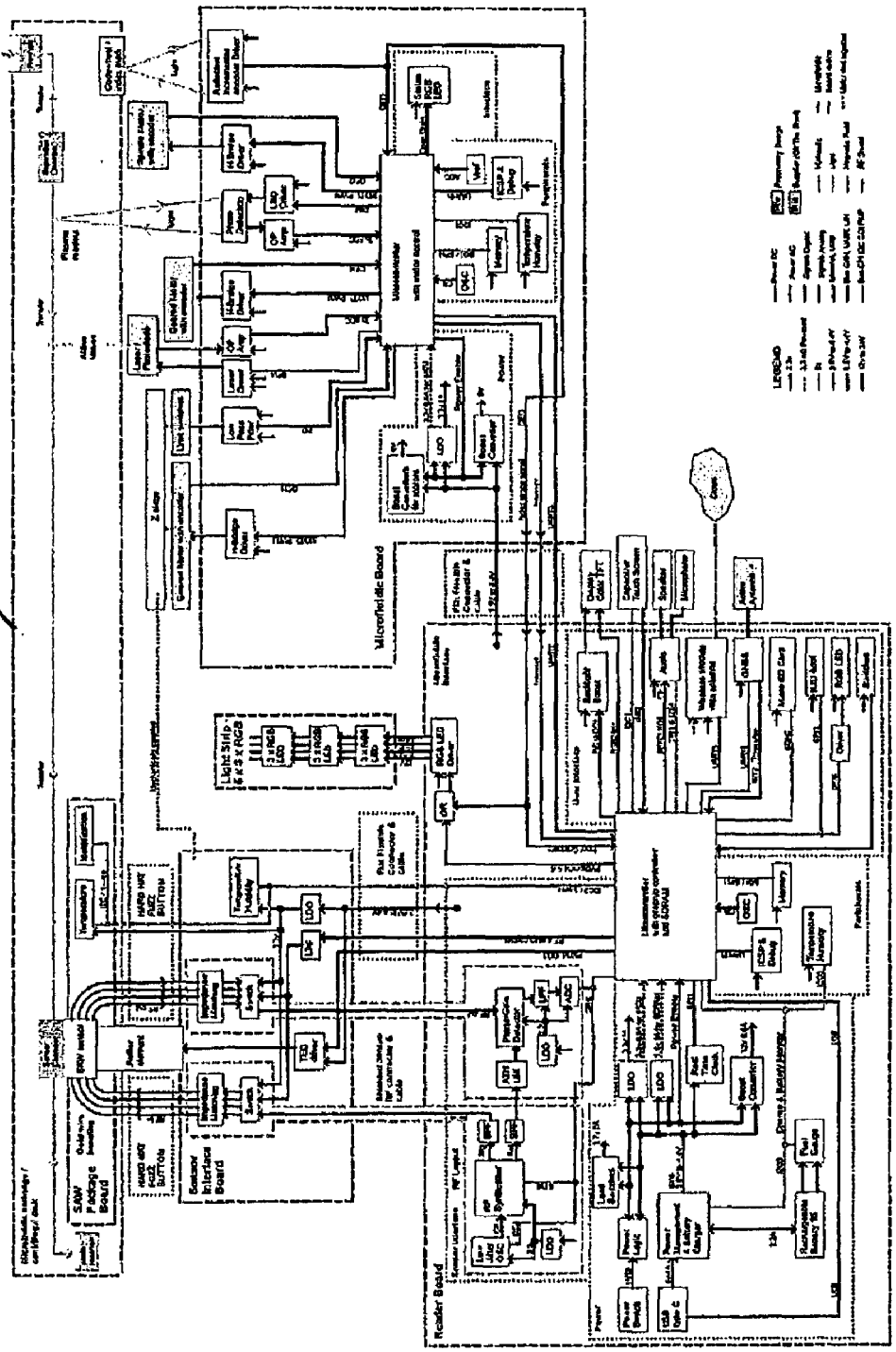

We claim:

1. An automated method in a cloud-based ecosystem of diagnostically field testing a sample taken from a subject in a portable handheld instrument to determine the presence of viral antigens and/or antibodies thereto comprising:

disposing the sample into a receiving chamber in a rotatable disc in the instrument;

processing under automated control of the sample in the rotatable disc using the instrument according to a nature of the sample and a corresponding means of detection in the portable handheld instrument of the viral antigens and/or antibodies subject to diagnostic testing;

detecting under automated control a quantitative measure of the viral antigens and/or antibodies in the sample using the corresponding means of detection in the portable handheld instrument;

generating under automated control a data output of the detected quantitative measure of the viral antigens and/or antibodies in the sample corresponding to the subject;

communicating under automated control the data output corresponding to the subject to a cloud-based database;

comparatively analyzing under automated control in a cloud based ecosystem the communicated data output corresponding to the subject relative to a plurality of different types of viral antigens and/or antibodies to diagnose a type of viral infection, if any, the subject most likely carries or has previously carried; and communicating under automated control results of the comparative analysis to the subject from the cloud-based ecosystem, where comparatively analyzing under automated control in a cloud based ecosystem the communicated data output corresponding to the subject relative to a plurality of different types of viral antigens and/or antibodies to diagnose the type of viral infection, if any, the subject most likely carries or has previously carried comprises:

analyzing under automated control the communicated data output for positive and/or negative indications of Covid-19 antigens and/or antibodies;

comparing under automated control the communicated data output for positive and/or negative indications of Covid-19 to communicated data output for positive and/or negative indications of a microarray for a plurality of viral infections sharing at least some of the Covid-19 antigens and/or antibodies; and determining under automated control whether the communicated data output of positive and/or negative indications of Covid-19 are statistically indicative of Covid-19 rather than the plurality of viral infections sharing at least some of the Covid-19 antigens and/or antibodies, so that false positives and/or false negatives are substantially reduced.

2. The automated method of claim 1 where determining under automated control whether the communicated data output of positive and/or negative indications of Covid-19 are statistically indicative of Covid-19 rather than the plurality of viral infections sharing at least some of the Covid-19 antigens and/or antibodies comprises determining under automated control whether corresponding Z-scores of the communicated data output of positive and/or negative indications of Covid-19 are indicative of Covid-19 rather than Z-scores of the plurality of viral infections sharing at least some of the Covid-19 antigens and/or antibodies.

3. The automated method of claim 1 where comparing under automated control the communicated data output for positive and/or negative indications of Covid-19 to communicated data output for positive and/or negative indications of the microarray for a plurality of viral infections sharing at least some of the Covid-19 antigens and/or antibodies comprises comparing under automated control the communicated data output for positive and/or negative indications of Covid-19 to communicated data output for positive and/or negative indications of a microarray for a plurality of acute respiratory infections selected from the group including SARS-CoV-2, SARS-CoV, MERS-CoV, common cold coronaviruses (including HKU1, OC43, NL63, and 229E), and multiple subtypes of influenza, adenovirus, metapneumovirus, parainfluenza, and/or respiratory syncytial virus.

4. The automated method of claim 1 where the means of detection comprises a microarray of antigen and/or antibody fluorescent spots and where detecting under automated control a quantitative measure of the viral antigens and/or antibodies in the sample using the corresponding means of detection in the instrument comprises generating under automated control an image file of a color image of the microarray of antigen and/or antibody fluorescent spots.

5. The automated method of claim 1 where processing under automated control the sample in the rotatable disc using the instrument according to the nature of the sample and the corresponding means of detection in the instrument of the viral antigens and/or antibodies subject to diagnostic testing comprises performing under automated control an ELISA blood test check for immunoglobulin G (IgG) and for Immunoglobin M (IgM) antibodies.

6. The automated method of claim 1 where processing under automated control the sample in the rotatable disc using the instrument according to the nature of the sample and the corresponding means of detection in the instrument of the viral antigens and/or antibodies subject to diagnostic testing comprises performing under automated control an immunofluorescence assay using a conjugated fluorescent label by direct or indirect immunofluorescence wherein an amount of conjugation of an antibody to an antigen is directly correlated with an amount of the fluorescence produced source.

7. An automated cloud-based system for diagnostically field testing a sample taken from a subject using an automated portable handheld instrument to determine a presence of viral antigens and/or antibodies thereto comprising:

a sample receiving chamber in a rotatable disc in the instrument;

a reader for automatically processing the sample in the rotatable disc using the instrument according to a nature of the sample and a corresponding means of detection in the portable handheld instrument of the viral antigens and/or antibodies subject to diagnostic testing;

a detector for automatically detecting a quantitative measure of the viral antigens and/or antibodies in the sample using the corresponding means of detection in the portable handheld instrument;

a data output circuit for automatically generating the detected quantitative measure of the viral antigens and/or antibodies in the sample corresponding to the subject;

a communication circuit for automatically communicating the data output corresponding to the subject to a cloud-based database;

a cloud based ecosystem configured to comparatively analyze under automated control the communicated data output corresponding to the subject relative to a plurality of different types of viral antigens and/or antibodies to diagnose the type of viral infection, if any, the subject most likely carries or has previously carried, and for automatically communicating the results of the comparative analysis to the subject from the cloud based ecosystem, where the cloud based ecosystem configured to comparatively analyze under automated control the communicated data output corresponding to the subject relative to a plurality of different types of viral antigens and/or antibodies to diagnose type of viral infection, if any, the subject most likely carries or has previously carried comprises a cloud-based module configured to automatically analyze the communicated data output of the microarray for positive and/or negative indications of Covid-19 antigens and/or antibodies, to automatically compare the communicated data output for positive and/or negative indications of Covid-19 to communicated data output for positive and/or negative indications of a microarray for a plurality of viral infections sharing at least some of the Covid-19 antigens and/or antibodies, and to automatically determine whether the communicated data output of positive and/or negative indications of Covid-19 are statistically indicative of Covid-19 rather than the plurality of viral infections sharing at least some of the Covid-19 antigens and/or antibodies, so that false positives and/or false negatives are substantially reduced.

8. The automated cloud-based system of claim 7 where the cloud-based module configured to automatically determine whether the communicated data output of positive and/or negative indications of Covid-19 are statistically indicative of Covid-19 rather than the plurality of viral infections sharing at least some of the Covid-19 antigens and/or antibodies comprises a cloud-based module configured to automatically determine under automated control whether corresponding Z-scores of the communicated data output of positive and/or negative indications are indicative of Covid-19 rather than Z-scores of the plurality of viral infections sharing at least some of the Covid-19 antigens and/or antibodies.

9. The automated cloud-based system of claim 7 where the cloud-based module configured to automatically compare under automated control the communicated data output for positive and/or negative indications of Covid-19 to communicated data output for positive and/or negative indications of the microarray for a plurality of viral infections sharing at least some of the Covid-19 antigens and/or antibodies comprises a cloud based module configured to automatically compare the communicated data output for positive and/or negative indications of Covid-19 to communicated data output for positive and/or negative indications of the microarray for a plurality of acute respiratory infections selected from a group including SARS-CoV-2, SARS-CoV, MERS-CoV, common cold coronaviruses (including HKU1, OC43, NL63, and 229E), and multiple subtypes of influenza, adenovirus, metapneumovirus, parainfluenza, and/or respiratory syncytial virus.

10. The automated cloud-based system of claim 7 where the cloud-based module configured to automatically determine whether the communicated data output of positive and/or negative indications of Covid-19 are statistically indicative of Covid-19 rather than the plurality of viral infections sharing at least some of the Covid-19 antigens and/or antibodies, so that false positives and/or false negatives are substantially reduced comprises a cloud based module configured to automatically determine under automated control sensitivity and specificity for Covid-19 from a combination of a plurality of antigens based on a corresponding Youden Index calculated for the combination of plurality of antigens.

* * * * *